(12) United States Patent
Ono et al.

(10) Patent No.: US 9,518,282 B2
(45) Date of Patent: Dec. 13, 2016

(54) METHOD FOR UTILIZING MONOTERPENE GLYCOSYLTRANSFERASE

(75) Inventors: Eiichiro Ono, Osaka (JP); Nobuo Tsuruoka, Ibaraki (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 560 days.

(21) Appl. No.: 13/997,683

(22) PCT Filed: Dec. 27, 2011

(86) PCT No.: PCT/JP2011/080584
§ 371 (c)(1),
(2), (4) Date: Jun. 25, 2013

(87) PCT Pub. No.: WO2012/091165
PCT Pub. Date: Jul. 5, 2012

(65) Prior Publication Data
US 2014/0020137 A1    Jan. 16, 2014

(30) Foreign Application Priority Data
Dec. 28, 2010    (JP) .................................. 2010-293237

(51) Int. Cl.
*C12N 9/10*    (2006.01)
*C12N 15/09*    (2006.01)
(Continued)

(52) U.S. Cl.
CPC ............... *C12P 19/44* (2013.01); *A23L 27/36* (2016.08); *A61K 8/602* (2013.01); *A61K 8/64* (2013.01);
(Continued)

(58) Field of Classification Search
CPC ...... C12N 9/1051; C12N 15/8257; A61K 8/64
See application file for complete search history.

(56) References Cited

U.S. PATENT DOCUMENTS

| 2004/0161819 A1* | 8/2004 | Aharoni ............... C12N 9/1085 435/69.1 |
| 2007/0124832 A1* | 5/2007 | Lim ..................... C12N 9/1048 800/278 |
| 2010/0143975 A1* | 6/2010 | Caputi ............... C12N 15/8257 435/74 |

FOREIGN PATENT DOCUMENTS

| WO | WO-9711184 A1 | 3/1997 |
| WO | WO-2008062165 A2 | 5/2008 |

OTHER PUBLICATIONS

Boots et al., Health effects of quercetin: from antioxidant to nutraceutical. European journal of pharmacology 585.2 (2008): 325-337.*

(Continued)

*Primary Examiner* — Russell Kallis
*Assistant Examiner* — Fan Weihua
(74) *Attorney, Agent, or Firm* — Drinker Biddle & Reath LLP

(57) ABSTRACT

The object of the present invention is to provide a novel method for producing a terpene 8-glycoside.

The present invention provides a method for producing a terpene 8-glycoside by means of glycosyltransferase acting on the 8-position of terpenes. The present invention provides a transformant transformed with a gene for the glycosyltransferase acting on the 8-position of terpenes and a method for producing such a transformant. The present invention provides a plant modified to suppress the expression of a protein having glycosylation activity on the 8-position of a monoterpene compound.

9 Claims, 12 Drawing Sheets

(51) Int. Cl.
| | |
|---|---|
| C12N 15/82 | (2006.01) |
| C12P 19/18 | (2006.01) |
| A23B 9/00 | (2006.01) |
| A23L 1/00 | (2006.01) |
| A61K 36/31 | (2006.01) |
| C12P 19/44 | (2006.01) |
| A61K 8/60 | (2006.01) |
| A61Q 19/00 | (2006.01) |
| A61K 8/64 | (2006.01) |

(52) U.S. Cl.
CPC ............ *A61Q 19/00* (2013.01); *C12N 9/1048* (2013.01); *C12N 9/1051* (2013.01); *C12N 15/8257* (2013.01); *C12P 19/18* (2013.01); *C12Y 204/01* (2013.01); *Y02P 20/52* (2015.11)

(56) References Cited

OTHER PUBLICATIONS

Encyclopedia of life, http: //eol.org/pages/583954/overview.*
Woo, Ho-Hyung, et al. "Modifying expression of closely related UDP-glycosyltransferases from pea and Arabidopsis results in altered root development and function." Physiologia plantarum 130.2 (2007): 250-260.*
Waterhouse, Peter M., and Christopher A. Helliwell. "Exploring plant genomes by RNA-induced gene silencing." Nature Reviews Genetics 4.1 (2003): 29-38.*
Koga, Asami, et al. "Characterization of T-DNA insertion mutants and RNAi silenced plants of Arabidopsis thaliana UV-damaged DNA binding protein 2 (AtUV-DDB2)." Plant molecular biology 61.1-2 (2006): 227-240.*
Krysan, Patrick J., Jeffery C. Young, and Michael R. Sussman. "T-DNA as an insertional mutagen in Arabidopsis." The Plant Cell 11.12 (1999): 2283-2290.*
NCBI Reference Sequence: NP_173655.2, "UDP-glucosyll transferase 85A3 [Arabidopsis thaliana]." Jan. 22, 2014, Abstract.
International Search Report mailed Mar. 19, 2012 issued in PCT Application No. PCT/JP201/080584 filed Dec. 27, 2011.
Aharoni, et al., "Terpenoid Metabolism in Wild-Type and Transgenic Arabidopsis Plants", Plant Cell, Dec. 2003, vol. 15, pp. 2866-2884.
Kollmannsberger, et al., "Occurrence of Glycosidically bound flavor compounds in hops, hop products and beer", Mschr. Brauwissenshaft, 2008, vol. 59, pp. 83-89.
Guo, et al., "(S)-Linalyl, 2-Phenylethyl, and Benzyl Disaccharide Glyosides Isolated as Aroma Precursors from Oolong Tea Leaves", Biosci. Biotech. Biochem., 1994, vol. 58, No. 8, pp. 1532-1534.
Nishikitani, et al., "Geranyl 6-O-x-L-Arabinopyranosyl-β-D-glucopyranoside Isolated as an Aroma Precursor from leaves of a Green Tea Cultivar", Biosci. Biotech. Biochem., 1996, vol. 60, No. 5, pp. 929-931.
Moon, et al., "*cis*- and *trans*-Linalool 3,7-Oxides and Methyl Salicylate Glycosides and (Z)-3-Hexenyl β-D-Glucopuranoside as Aroma Precursors from Tea Leaves for Oolong Tea", Biosci. Biotech. Biochem., 1996, vol. 60, No. 11, pp. 1815-1819.
Ma, et al., "The (3R, 9R)-3-hydroxy-7,8-dihydro-βionol disaccharide glycoside is an aroma precursor in tea leaves", Phytochemistry, 2001, vol. 56, pp. 819-825.
Sekiwa, et al., "Isolation of Some Glucosides as Aroma Precursor from Ginger", Biosci. Biotechnol. Biochem., 1999, vol. 63, No. 2, pp. 384-389.
Winterhalter, et al., "Glycoconjugated Aroma Compounds: Occurrence, Role and Biotechnological Transformation", Adv. Biochem. Eng. Biotechnol., 1997, vol. 55, pp. 73-105.
Andreas Hermann, "Controlled Release of Volatiles under Mild Reaction Conditions: From Nature to Everyday Products", Angew. Chem. Int. Ed., 2007, vol. 46, pp. 5836-5863.
Mizutani, et al., "Cloning of β-Primeverosidase from Tea Leaves, a Key Enzyme in Tea Aroma Formation", Plant Physiology, Dec. 2002, vol. 130, pp. 2164-2176.
Caputi, et al., "Discovery of New Biocatalysts for the Glycosylation of Terpenoid Scaffolds", Chem. Eur. J., 2008, vol. 14, pp. 6656-6662.
Fan, et al., "Characterization of three terpenoid glycosyltransferase genes in 'Valencia' sweet orange (*Citrus sinensis* L. (Osbeck)", Genome, 2010, vol. 53, pp. 816-823.
Winter, et al., "An "Electronic Flouorescent Pictograph" Browser for Exploring and Analyzing Large-Scale Biological Data Sets", PLos One, Aug. 2008, vol. 2, Issue 8, e718.
Hou, et al., "*N*-Glucosylation of Cytokinins by Glycosyltransferases of *Arabidopsis thaliana*", The Journal of Biological Chemistry, 2004, vol. 279, No. 46, pp. 47822-47832.
Kristensen, et al., "Metabolic engineering of dhurrin in transgenic *Arabidopsis* plants with marginal inadvertent effects on the metabolome and transcriptome", Proc. Natl. Acd. Sci. USA, Feb. 1, 2005, vol. 102, No. 5, pp. 1779-1784.
Franks, et al., "A seed coat cyanohydrin glucosyltransferase is associated with bitterness in almond (*Prunus dulcis*) kernels", Functional Plant Biology, 2008, vol. 35, pp. 236-246.
Woo, et al., "Characterization of *Arabidopsis* AtUGT85A and AtGUS gene families and their expression in rapidly dividing tissues", Genomics, 2007, vol. 90, pp. 143-153.
EP Application No. 11853650.7—Extended European Search Report issued Mar. 16, 2016.
Efraim Lewinsohn et al., "Phytochemical diversity: The sounds of silent metabolism", Plant Science, Feb. 1, 2009, vol. 176, No. 2, pp. 161-169.
Junfeng Wang, et al., Cloning and Functional Analysis of Geraniol 10-Hydroxylase, a Cytochrome P450 from *swertia mussotii* Franch, Biosci. Biotechnol. Biochem., Aug. 23, 2010, vol. 74, No. 8, pp. 1583-1590.
René Höfer, et al., "Geraniol hydroxylase and hydroxygeraniol oxidase activites of the CYP76 family of cytochrome P450 enzymes and potential for engineering the early steps of the (seco)iridoid pathway", Metabolic Engineering, Nov. 1, 2013, vol. 20, pp. 221-232.

* cited by examiner

Figure 5

| substrate | Geraniol | 8-OH Geraniol | Linalool | 8-OH Linalool |
|---|---|---|---|---|
| Expected product | Geranyl β-D-glucopyranoside | 8-Hydoxy geranyl β-D-glucopyranoside | Linalyl β-D-glucopyranoside | 8-Hydoxy linalyl β-D-glucopyranoside |
| Chemical structure | (structure) | (structure) | (structure) | (structure) |
| Exact Mass: Mol. Wt.: | $C_{16}H_{28}O_6$ Exact Mass: 316.18859 Mol. Wt.: 316.38992 | $C_{16}H_{28}O_7$ Exact Mass: 332.18350 Mol. Wt.: 332.38932 | $C_{16}H_{28}O_6$ Exact Mass: 316.18859 Mol. Wt.: 316.38992 | $C_{16}H_{28}O_7$ Exact Mass: 332.18350 Mol. Wt.: 332.38932 |
| ESI-MS (negative mode) | m/z 315 [M-H]⁻, 338 [M+Na-H]⁻, 361 [M+HCOOH-H]⁻ | m/z 331 [M-H]⁻, 354 [M+Na-H]⁻, 377 [M+HCOOH-H]⁻ | m/z 315 [M-H]⁻, 338 [M+Na-H]⁻, 361 [M+HCOOH-H]⁻ | m/z 331 [M-H]⁻, 354 [M+Na-H]⁻, 377 [M+HCOOH-H]⁻ |
| Authentic standard | in house synthesis | none | in house synthesis | In house synthesis |

SEQUENCE LISTING

```
<160> NUMBER OF SEQ ID NOS: 13

<210> SEQ ID NO 1
<211> LENGTH: 1464
<212> TYPE: DNA
<213> ORGANISM: Arabidopsis thaliana
<220> FEATURE:
<221> NAME/KEY: CDS
<222> LOCATION: (1)..(1464)

<400> SEQUENCE: 1 atg gga tcc cgt ttt gtt tct aac gaa caa aaa cca cac gta gtt tgc      48
Met Gly Ser Arg Phe Val Ser Asn Glu Gln Lys Pro His Val Val Cys
1               5                   10                  15 gtg cct tac cca gct caa ggc cac att aac cct atg atg aaa gtg gct      96
Val Pro Tyr Pro Ala Gln Gly His Ile Asn Pro Met Met Lys Val Ala
                20                  25                  30 aaa ctc ctc cac gtc aaa ggc ttc cac gtc acc ttc gtc aac acc gtc     144
Lys Leu Leu His Val Lys Gly Phe His Val Thr Phe Val Asn Thr Val
            35                  40                  45 tac aac cac aac cgt cta ctc cga tcc cgt ggg gcc aac gca ctc gat     192
Tyr Asn His Asn Arg Leu Leu Arg Ser Arg Gly Ala Asn Ala Leu Asp
        50                  55                  60 gga ctt cct tcc ttc cag ttc gag tca ata cct gac ggt ctt ccg gag     240
Gly Leu Pro Ser Phe Gln Phe Glu Ser Ile Pro Asp Gly Leu Pro Glu
65                  70                  75                  80 act ggc gtg gac gcc acg cag gac atc cct gcc ctt tcc gag tcc aca     288
Thr Gly Val Asp Ala Thr Gln Asp Ile Pro Ala Leu Ser Glu Ser Thr
                85                  90                  95 acg aaa aac tgt ctc gtt ccg ttc aag aag ctt ctc cag cgg att gtc     336
Thr Lys Asn Cys Leu Val Pro Phe Lys Lys Leu Leu Gln Arg Ile Val
                100                 105                 110 acg aga gag gat gtc cct ccg gtg agc tgt att gta tca gat ggt tcg     384
Thr Arg Glu Asp Val Pro Pro Val Ser Cys Ile Val Ser Asp Gly Ser
            115                 120                 125 atg agc ttt act ctt gac gta gcg gaa gag ctt ggt gtt ccg gag att     432
Met Ser Phe Thr Leu Asp Val Ala Glu Glu Leu Gly Val Pro Glu Ile
        130                 135                 140 cat ttt tgg acc act agt gct tgt ggc ttc atg gct tat cta cac ttt     480
His Phe Trp Thr Thr Ser Ala Cys Gly Phe Met Ala Tyr Leu His Phe
145                 150                 155                 160 tat ctc ttc atc gag aag ggt tta tgt cca gta aaa gat gcg agt tgc     528
Tyr Leu Phe Ile Glu Lys Gly Leu Cys Pro Val Lys Asp Ala Ser Cys
                165                 170                 175 ttg acg aag gaa tac ttg gac aca gtt ata gat tgg ata ccg tca atg     576
```

```
                Leu Thr Lys Glu Tyr Leu Asp Thr Val Ile Asp Trp Ile Pro Ser Met
                            180                 185                 190 aac aat gta aaa cta aaa gac att cct agt ttt ata cgt acc act aat       624
Asn Asn Val Lys Leu Lys Asp Ile Pro Ser Phe Ile Arg Thr Thr Asn
            195                 200                 205 cct aac gac ata atg ctc aac ttc gtt gtc cgt gag gca tgt cga acc       672
Pro Asn Asp Ile Met Leu Asn Phe Val Val Arg Glu Ala Cys Arg Thr
210                 215                 220 aaa cgt gcc tct gct atc att ctg aac acg ttt gat gac ctt gaa cat       720
Lys Arg Ala Ser Ala Ile Ile Leu Asn Thr Phe Asp Asp Leu Glu His
225                 230                 235                 240 gac ata atc cag tct atg caa tcc att tta cca ccg gtt tat cca atc       768
Asp Ile Ile Gln Ser Met Gln Ser Ile Leu Pro Pro Val Tyr Pro Ile
                245                 250                 255 gga ccg ctt cat ctc tta gta aac agg gag att gaa gaa gat agt gag       816
Gly Pro Leu His Leu Leu Val Asn Arg Glu Ile Glu Glu Asp Ser Glu
                260                 265                 270 att gga agg atg gga tca aat cta tgg aaa gag gag act gag tgc ttg       864
Ile Gly Arg Met Gly Ser Asn Leu Trp Lys Glu Glu Thr Glu Cys Leu
            275                 280                 285 gga tgg ctt aat act aag tct cga aat agc gtt gtt tat gtt aac ttt       912
Gly Trp Leu Asn Thr Lys Ser Arg Asn Ser Val Val Tyr Val Asn Phe
290                 295                 300 ggg agc ata aca ata atg acc acg gca cag ctt ttg gag ttt gct tgg       960
Gly Ser Ile Thr Ile Met Thr Thr Ala Gln Leu Leu Glu Phe Ala Trp
305                 310                 315                 320 ggt ttg gcg gca acg gga aag gag ttt cta tgg gtg atg cgg ccg gat      1008
Gly Leu Ala Ala Thr Gly Lys Glu Phe Leu Trp Val Met Arg Pro Asp
                325                 330                 335 tca gta gcc gga gag gag gca gtg att cca aaa gag ttt tta gcg gag      1056
Ser Val Ala Gly Glu Glu Ala Val Ile Pro Lys Glu Phe Leu Ala Glu
                340                 345                 350 aca gct gat cga aga atg ctg aca agt tgg tgt cct cag gag aaa gtt      1104
Thr Ala Asp Arg Arg Met Leu Thr Ser Trp Cys Pro Gln Glu Lys Val
            355                 360                 365 ctt tct cat ccg gcg gtc gga ggg ttc ttg acc cat tgc ggg tgg aat      1152
Leu Ser His Pro Ala Val Gly Gly Phe Leu Thr His Cys Gly Trp Asn
370                 375                 380 tcg acg tta gaa agt ctt tca tgc gga gtt cca atg gta tgt tgg cca      1200
Ser Thr Leu Glu Ser Leu Ser Cys Gly Val Pro Met Val Cys Trp Pro
385                 390                 395                 400 ttt ttt gct gag caa caa aca aat tgt aag ttt tct tgt gat gaa tgg      1248
Phe Phe Ala Glu Gln Gln Thr Asn Cys Lys Phe Ser Cys Asp Glu Trp
                405                 410                 415 gag gtt ggt att gag atc ggt gga gat gtc aag agg gga gag gtt gag      1296
Glu Val Gly Ile Glu Ile Gly Gly Asp Val Lys Arg Gly Glu Val Glu
                420                 425                 430 gcg gtg gtt aga gag ctc atg gat gga gag aaa gga aag aaa atg aga      1344
Ala Val Val Arg Glu Leu Met Asp Gly Glu Lys Gly Lys Lys Met Arg
            435                 440                 445 gag aag gct gta gag tgg cgg cgc ttg gcc gag aaa gct aca aag ctt      1392
Glu Lys Ala Val Glu Trp Arg Arg Leu Ala Glu Lys Ala Thr Lys Leu
450                 455                 460 ccg tgt ggt tcg tcg gtg ata aat ttt gag acg att gtc aac aag gtt      1440
Pro Cys Gly Ser Ser Val Ile Asn Phe Glu Thr Ile Val Asn Lys Val
465                 470                 475                 480 ctc ttg gga aag atc cct aac acg                                      1464
Leu Leu Gly Lys Ile Pro Asn Thr
                485
```

<210> SEQ ID NO 2
<211> LENGTH: 488
<212> TYPE: PRT
<213> ORGANISM: Arabidopsis thaliana

<400> SEQUENCE: 2

```
Met Gly Ser Arg Phe Val Ser Asn Glu Gln Lys Pro His Val Val Cys
1               5                   10                  15

Val Pro Tyr Pro Ala Gln Gly His Ile Asn Pro Met Met Lys Val Ala
            20                  25                  30

Lys Leu Leu His Val Lys Gly Phe His Val Thr Phe Val Asn Thr Val
        35                  40                  45

Tyr Asn His Asn Arg Leu Leu Arg Ser Arg Gly Ala Asn Ala Leu Asp
    50                  55                  60

Gly Leu Pro Ser Phe Gln Phe Glu Ser Ile Pro Asp Gly Leu Pro Glu
65                  70                  75                  80

Thr Gly Val Asp Ala Thr Gln Asp Ile Pro Ala Leu Ser Glu Ser Thr
                85                  90                  95

Thr Lys Asn Cys Leu Val Pro Phe Lys Lys Leu Leu Gln Arg Ile Val
            100                 105                 110

Thr Arg Glu Asp Val Pro Pro Val Ser Cys Ile Val Ser Asp Gly Ser
        115                 120                 125

Met Ser Phe Thr Leu Asp Val Ala Glu Glu Leu Gly Val Pro Glu Ile
130                 135                 140

His Phe Trp Thr Thr Ser Ala Cys Gly Phe Met Ala Tyr Leu His Phe
145                 150                 155                 160

Tyr Leu Phe Ile Glu Lys Gly Leu Cys Pro Val Lys Asp Ala Ser Cys
                165                 170                 175

Leu Thr Lys Glu Tyr Leu Asp Thr Val Ile Asp Trp Ile Pro Ser Met
            180                 185                 190

Asn Asn Val Lys Leu Lys Asp Ile Pro Ser Phe Ile Arg Thr Thr Asn
        195                 200                 205

Pro Asn Asp Ile Met Leu Asn Phe Val Val Arg Glu Ala Cys Arg Thr
    210                 215                 220

Lys Arg Ala Ser Ala Ile Ile Leu Asn Thr Phe Asp Asp Leu Glu His
225                 230                 235                 240

Asp Ile Ile Gln Ser Met Gln Ser Ile Leu Pro Pro Val Tyr Pro Ile
                245                 250                 255

Gly Pro Leu His Leu Leu Val Asn Arg Glu Ile Glu Glu Asp Ser Glu
            260                 265                 270

Ile Gly Arg Met Gly Ser Asn Leu Trp Lys Glu Glu Thr Glu Cys Leu
        275                 280                 285

Gly Trp Leu Asn Thr Lys Ser Arg Asn Ser Val Val Tyr Val Asn Phe
    290                 295                 300

Gly Ser Ile Thr Ile Met Thr Thr Ala Gln Leu Leu Glu Phe Ala Trp
305                 310                 315                 320

Gly Leu Ala Ala Thr Gly Lys Glu Phe Leu Trp Val Met Arg Pro Asp
                325                 330                 335

Ser Val Ala Gly Glu Glu Ala Val Ile Pro Lys Glu Phe Leu Ala Glu
            340                 345                 350

Thr Ala Asp Arg Arg Met Leu Thr Ser Trp Cys Pro Gln Glu Lys Val
        355                 360                 365

Leu Ser His Pro Ala Val Gly Gly Phe Leu Thr His Cys Gly Trp Asn
    370                 375                 380
```

```
Ser Thr Leu Glu Ser Leu Ser Cys Gly Val Pro Met Val Cys Trp Pro
385                 390                 395                 400

Phe Phe Ala Glu Gln Gln Thr Asn Cys Lys Phe Ser Cys Asp Glu Trp
                405                 410                 415

Glu Val Gly Ile Glu Ile Gly Gly Asp Val Lys Arg Gly Glu Val Glu
            420                 425                 430

Ala Val Val Arg Glu Leu Met Asp Gly Glu Lys Gly Lys Lys Met Arg
            435                 440                 445

Glu Lys Ala Val Glu Trp Arg Arg Leu Ala Glu Lys Ala Thr Lys Leu
        450                 455                 460

Pro Cys Gly Ser Ser Val Ile Asn Phe Glu Thr Ile Val Asn Lys Val
465                 470                 475                 480

Leu Leu Gly Lys Ile Pro Asn Thr
                485

<210> SEQ ID NO 3
<211> LENGTH: 1811
<212> TYPE: DNA
<213> ORGANISM: Arabidopsis thaliana

<400> SEQUENCE: 3
ttacgtgtta gggatctttc ccaagagaac cttgttgaca atcgtctcaa aatttatcac      60
cgacgaacca cacggaagct tgtagctttc tcggccaag cgccgccact ctacagcctt     120
ctctctcatt ttctttcctt tctctccatc catgagctct ctaaccaccg cctcaacctc     180 tccctcttg acatctccac cgatctcaat accaacctcc cattcatcac aagaaaactt     240
acaatttgtt tgttgctcag caaaaaatgg ccaacatacc attggaactc cgcatgaaag     300
actttctaac gtcgaattcc acccgcaatg ggtcaagaac cctccgaccg ccggatgaga     360
aagaactttc tcctgaggac accaacttgt cagcattctt cgatcagctg tctccgctaa     420
aaactctttt ggaatcactg cctcctctcc ggctactgaa tccggccgca tcacccatag     480
aaactccttt cccgttgccg ccaaaccca agcaaactcc aaaagctgtg ccgtggtcat     540
tattgttatg ctcccaaagt taacataaac aacgctattt cgagacttag tattaagcca     600
tcccaagcac tcagtctcct cttttccatag atttgatccc atccttccaa tctcactatc     660
ttcttcaatc tccctgttta ctaagagatg aagcggtccg attggataaa ccggtggtaa     720
aatggattgc atagactgga ttatgtcatg ttcaaggtca tcaaacgtgt tcagaatgat     780
agcagaggca cgtttggttc gacatgcctc acggacaacg aagttgagca ttatgtcgtt     840
aggattagtg gtacgtataa aactaggaat gtcttttagt tttacattgt tcattgacgg     900
tatccaatct ataactgtgt ccaagtattc cttcgtcaag caactcgcat ctgcaaaatc     960
catcacactt tatttttatca ttttatctct caatatttat ttataaaatt aatgcacaga    1020
cttagcatac acaatttaat gtattttata gtgatagtct tgtttcagag ctagttggca    1080
aacaaatggc ttagagagtg atgttggcct atttgcatta agctttattt atggttgtac    1140
tttgagattc ggttaaataa gagttctagg ccaacatcac tttctaggcc taattgcaaa    1200
taaagtgacc aagctcatgg tgtcttaaga gttcttacgt gaaatttat ttataacgt      1260 cgattaattc aataataaat gcaagaaaac gtacctttta ctggacataa acccttctcg    1320
atgaagagat aaaagtgtag ataagccatg aagccacaag cactagtggt ccaaaaatga    1380
atctccggaa caccaagctc ttccgctacg tcaagagtaa agctcatcga accatctgat    1440
acaatacagc tcaccggagg gacatcctct ctcgtgacaa tccgctggag aagcttcttg    1500
```

```
aacggaacga gacagttttt cgttgtggac tcggaaaggg cagggatgtc ctgcgtggcg    1560
tccacgccag tctccggaag accgtcaggt attgactcga actggaagga aggaagtcca    1620
tcgagtgcgt tggccccacg ggatcggagt agacggttgt ggttgtagac ggtgttgacg    1680
aaggtgacgt ggaagccttt gacgtggagg agtttagcca ctttcatcat agggttaatg    1740
tggccttgag ctgggtaagg cacgcaaact acgtgtggtt tttgttcgtt agaaacaaaa    1800
cgggatccca t                                                        1811

<210> SEQ ID NO 4
<211> LENGTH: 1467
<212> TYPE: DNA
<213> ORGANISM: Arabidopsis thaliana

<400> SEQUENCE: 4
atgggatccc gttttgtttc taacgaacaa aaaccacacg tagtttgcgt gccttaccca     60
gctcaaggcc acattaaccc tatgatgaaa gtggctaaac tcctccacgt caaaggcttc    120
cacgtcacct tcgtcaacac cgtctacaac cacaaccgtc tactccgatc ccgtggggcc    180
aacgcactcg atggacttcc ttccttccag ttcgagtcaa tacctgacgg tcttccggag    240
actggcgtgg acgccacgca ggacatccct gcccttttcg agtccacaac gaaaaactgt    300
ctcgttccgt tcaagaagct tctccagcgg attgtcacga gagaggatgt ccctccggtg    360
agctgtattg tatcagatgg ttcgatgagc tttactcttg acgtagcgga agagcttggt    420
gttccggaga ttcattttg gaccactagt gcttgtggct tcatggctta tctacacttt    480
tatctcttca tcgagaaggg tttatgtcca gtaaaagatg cgagttgctt gacgaaggaa    540
tacttggaca cagttataga ttggataccg tcaatgaaca atgtaaaact aaaagacatt    600
cctagtttta tacgtaccac taatcctaac gacataatgc tcaacttcgt tgtccgtgag    660
gcatgtcgaa ccaaacgtgc ctctgctatc attctgaaca cgtttgatga ccttgaacat    720
gacataatcc agtctatgca atccatttta ccaccggttt atccaatcgg accgcttcat    780
ctcttagtaa acaggagat tgaagaagat agtgagattg aaggatggg atcaaatcta    840 tggaaagagg agactgagtg cttgggatgg cttaatacta agtctcgaaa tagcgttgtt    900
tatgttaact ttgggagcat aacaataatg accacggcac agcttttgga gtttgcttgg    960
ggtttggcgg caacgggaaa ggagtttcta tgggtgatgc ggccggattc agtagccgga   1020
gaggaggcag tgattccaaa agagttttta gcggagacag ctgatcgaag aatgctgaca   1080
agttggtgtc ctcaggagaa agttctttct catccggcgg tcgagggtt cttgacccat   1140 tgcgggtgga attcgacgtt agaaagtctt tcatgcggag ttccaatggt atgttggcca   1200
ttttttgctg agcaacaaac aaattgtaag ttttcttgtg atgaatggga ggttggtatt   1260
gagatcggtg gagatgtcaa gaggggagag gttgaggcgg tggttagaga gctcatggat   1320
ggagagaaag gaaagaaaat gagagagaag gctgtagagt ggcggcgctt ggccgagaaa   1380
gctacaaagc ttccgtgtgg ttcgtcggtg ataaattttg agacgattgt caacaaggtt   1440
ctcttgggaa agatccctaa cacgtaa                                       1467

<210> SEQ ID NO 5
<211> LENGTH: 1467
<212> TYPE: DNA
<213> ORGANISM: Arabidopsis thaliana

<400> SEQUENCE: 5
```

```
atgggatccc gttttgtttc taacgaacaa aaaccacacg tagtttgcgt gccttaccca      60
gctcaaggcc acattaaccc tatgatgaaa gtggctaaac tcctccacgt caaaggcttc     120
cacgtcacct tcgtcaacac cgtctacaac cacaaccgtc tactccgatc ccgtggggcc     180
aacgcactcg atggacttcc ttccttccag ttcgagtcaa tacctgacgg tcttccggag     240
actggcgtgg acgccacgca ggacatccct gcccttccg agtccacaac gaaaaactgt      300
ctcgttccgt tcaagaagct ctccagcgg attgtcacga gagaggatgt ccctccggtg      360
agctgtattg tatcagatgg ttcgatgagc tttactcttg acgtagcgga agagcttggt     420
gttccggaga ttcattttg gaccactagt gcttgtggct tcatggctta tctacacttt      480
tatctcttca tcgagaaggg tttatgtcca gtaaaagatg cgagttgctt gacgaaggaa     540
tacttggaca cagttataga ttggataccg tcaatgaaca atgtaaaact aaaagacatt     600 cctagttta tacgtaccac taatcctaac gacataatgc tcaacttcgt tgtccgtgag      660
gcatgtcgaa ccaaacgtgc ctctgctatc attctgaaca cgtttgatga ccttgaacat     720
gacataatcc agtctatgca atccatttta ccaccggttt atccaatcgg accgcttcat     780
ctcttagtaa acagggagat tgaagaagat agtgagattg aaggatggg atcaaatcta      840 tggaaagagg agactgagtg cttgggatgg cttaatacta agtctcgaaa tagcgttgtt     900
tatgttaact ttgggagcat aacaataatg accacggcac agcttttgga gtttgcttgg     960
ggtttggcgc aacgggaaa ggagtttcta tgggtgatgc ggccggattc agtagccgga     1020
gaggaggcag tgattccaaa agagttttta gcggagacag ctgatcgaag aatgctgaca     1080
agttggtgtc ctcaggagaa agttcttct catccggcgg tcggaggggt cttgacccat     1140
tgcgggtgga attcgacgtt agaaagtctt tcatgcggag ttccaatggt atgttggcca     1200
ttttttgctg agcaacaaac aaattgtaag ttttcttgtg atgaatggga ggttggtatt     1260
gagatcggtg gagatgtcaa gaggggagag gttgaggcgg tggttagaga gctcatggat     1320
ggagagaaag gaaagaaaat gagagagaag gctgtagagt ggcggcgctt ggccgagaaa     1380
gctacaaagc ttccgtgtgg ttcgtcggtg ataaattttg agacgattgt caacaaggtt     1440
ctcttgggaa agatccctaa cacgtaa                                        1467
```

<210> SEQ ID NO 6
<211> LENGTH: 27
<212> TYPE: DNA
<213> ORGANISM: Artificial
<220> FEATURE:
<223> OTHER INFORMATION: Synthetic DNA

<400> SEQUENCE: 6

```
cacccatatg ggatcccgtt ttgtttc                                          27
```

<210> SEQ ID NO 7
<211> LENGTH: 27
<212> TYPE: DNA
<213> ORGANISM: Artificial
<220> FEATURE:
<223> OTHER INFORMATION: Synthetic DNA

<400> SEQUENCE: 7

```
actcgagtta cgtgttaggg atctttc                                          27
```

<210> SEQ ID NO 8
<211> LENGTH: 1467
<212> TYPE: DNA
<213> ORGANISM: Arabidopsis thaliana

```
<220> FEATURE:
<221> NAME/KEY: CDS
<222> LOCATION: (1)..(1467)

<400> SEQUENCE: 8 atg gga tct cag atc att cat aac tca caa aaa cca cat gta gtt tgt      48
Met Gly Ser Gln Ile Ile His Asn Ser Gln Lys Pro His Val Val Cys
1               5                   10                  15 gtt cca tat ccg gct caa ggc cac atc aac cct atg atg aga gtg gct      96
Val Pro Tyr Pro Ala Gln Gly His Ile Asn Pro Met Met Arg Val Ala
            20                  25                  30 aaa ctc ctc cac gcc aga ggc ttc tac gtc acc ttc gtc aac acc gtc     144
Lys Leu Leu His Ala Arg Gly Phe Tyr Val Thr Phe Val Asn Thr Val
        35                  40                  45 tac aac cac aat cgt ttc ctt cgt tct cgt ggg tcc aat gcc cta gat     192
Tyr Asn His Asn Arg Phe Leu Arg Ser Arg Gly Ser Asn Ala Leu Asp
    50                  55                  60 gga ctt cct tcg ttc cga ttt gag tcc att gct gac ggt cta cca gag     240
Gly Leu Pro Ser Phe Arg Phe Glu Ser Ile Ala Asp Gly Leu Pro Glu
65                  70                  75                  80 aca gac atg gat gcc acg cag gac atc aca gct ctt tgc gag tcc acc     288
Thr Asp Met Asp Ala Thr Gln Asp Ile Thr Ala Leu Cys Glu Ser Thr
                85                  90                  95 atg aag aac tgt ctc gct ccg ttc aga gag ctt ctc cag cgg atc aac     336
Met Lys Asn Cys Leu Ala Pro Phe Arg Glu Leu Leu Gln Arg Ile Asn
            100                 105                 110 gct gga gat aat gtt cct ccg gta agc tgt att gta tct gac ggt tgt     384
Ala Gly Asp Asn Val Pro Pro Val Ser Cys Ile Val Ser Asp Gly Cys
        115                 120                 125 atg agc ttt act ctt gat gtt gcg gag gag ctt gga gtc ccg gag gtt     432
Met Ser Phe Thr Leu Asp Val Ala Glu Glu Leu Gly Val Pro Glu Val
    130                 135                 140 ctt ttt tgg aca acc agt ggc tgt gcg ttc ctg gct tat cta cac ttt     480
Leu Phe Trp Thr Thr Ser Gly Cys Ala Phe Leu Ala Tyr Leu His Phe
145                 150                 155                 160 tat ctc ttc atc gag aag ggc tta tgt ccg cta aaa gat gag agt tac     528
Tyr Leu Phe Ile Glu Lys Gly Leu Cys Pro Leu Lys Asp Glu Ser Tyr
                165                 170                 175 ttg acg aag gag tac tta gaa gac acg gtt ata gat ttt ata cca acc     576
Leu Thr Lys Glu Tyr Leu Glu Asp Thr Val Ile Asp Phe Ile Pro Thr
            180                 185                 190 atg aag aat gtg aaa cta aag gat att cct agc ttc ata cgt acc act     624
Met Lys Asn Val Lys Leu Lys Asp Ile Pro Ser Phe Ile Arg Thr Thr
        195                 200                 205 aat cct gat gat gtt atg att agt ttc gcc ctc cgc gag acc gag cga     672
Asn Pro Asp Asp Val Met Ile Ser Phe Ala Leu Arg Glu Thr Glu Arg
    210                 215                 220 gcc aaa cgt gct tct gct atc att cta aac aca ttt gat gac ctt gag     720
Ala Lys Arg Ala Ser Ala Ile Ile Leu Asn Thr Phe Asp Asp Leu Glu
225                 230                 235                 240 cat gat gtt gtt cat gct atg caa tct atc tta cct ccg gtt tat tca     768
His Asp Val Val His Ala Met Gln Ser Ile Leu Pro Pro Val Tyr Ser
                245                 250                 255 gtt gga ccg ctt cat ctc tta gca aac cgg gag att gaa gaa ggt agt     816
Val Gly Pro Leu His Leu Leu Ala Asn Arg Glu Ile Glu Glu Gly Ser
            260                 265                 270 gag att gga atg atg agt cga aat tta tgg aaa gag gag atg gag tgt     864
Glu Ile Gly Met Met Ser Arg Asn Leu Trp Lys Glu Glu Met Glu Cys
        275                 280                 285 ttg gat tgg ctt gat act aag act caa aat agt gtc att tat atc aac     912
Leu Asp Trp Leu Asp Thr Lys Thr Gln Asn Ser Val Ile Tyr Ile Asn
```

```
Leu Asp Trp Leu Asp Thr Lys Thr Gln Asn Ser Val Ile Tyr Ile Asn
    290                 295                 300 ttt ggg agc ata acg gtt ttg agt gtg aag cag ctt gtg gag ttt gct      960
Phe Gly Ser Ile Thr Val Leu Ser Val Lys Gln Leu Val Glu Phe Ala
305                 310                 315                 320 tgg ggt ttg gcg gga agt ggg aaa gag ttt tta tgg gtg atc cgg cca     1008
Trp Gly Leu Ala Gly Ser Gly Lys Glu Phe Leu Trp Val Ile Arg Pro
                325                 330                 335 gat tta gta gcg gga gag gag gct atg gtt ccg ccg gac ttt tta atg     1056
Asp Leu Val Ala Gly Glu Glu Ala Met Val Pro Pro Asp Phe Leu Met
            340                 345                 350 gag act aaa gac cgc agt atg cta gcg agt tgg tgt cct caa gag aaa     1104
Glu Thr Lys Asp Arg Ser Met Leu Ala Ser Trp Cys Pro Gln Glu Lys
        355                 360                 365 gta ctt tct cat cct gct att gga ggg ttt ttg acg cat tgc ggg tgg     1152
Val Leu Ser His Pro Ala Ile Gly Gly Phe Leu Thr His Cys Gly Trp
    370                 375                 380 aac tcg ata ttg gaa agt ctt tcg tgt gga gtt ccg atg gtg tgt tgg     1200
Asn Ser Ile Leu Glu Ser Leu Ser Cys Gly Val Pro Met Val Cys Trp
385                 390                 395                 400 cca ttt ttt gct gac cag caa atg aat tgt aag ttt tgt tgt gac gag     1248
Pro Phe Phe Ala Asp Gln Gln Met Asn Cys Lys Phe Cys Cys Asp Glu
                405                 410                 415 tgg gat gtt ggg att gag ata ggt gga gat gtg aag aga gag gaa gtt     1296
Trp Asp Val Gly Ile Glu Ile Gly Gly Asp Val Lys Arg Glu Glu Val
            420                 425                 430 gag gcg gtg gtt aga gag ctc atg gat gga gag aag gga aag aaa atg     1344
Glu Ala Val Val Arg Glu Leu Met Asp Gly Glu Lys Gly Lys Lys Met
        435                 440                 445 aga gaa aag gcg gta gag tgg cag cgc tta gcc gag aaa gcg acg gaa     1392
Arg Glu Lys Ala Val Glu Trp Gln Arg Leu Ala Glu Lys Ala Thr Glu
    450                 455                 460 cat aaa ctt ggt tct tcc gtt atg aat ttt gag acg gtt gtt agc aag     1440
His Lys Leu Gly Ser Ser Val Met Asn Phe Glu Thr Val Val Ser Lys
465                 470                 475                 480 ttt ctt ttg gga caa aaa tca cag gat                                 1467
Phe Leu Leu Gly Gln Lys Ser Gln Asp
                485

<210> SEQ ID NO 9
<211> LENGTH: 489
<212> TYPE: PRT
<213> ORGANISM: Arabidopsis thaliana

<400> SEQUENCE: 9

Met Gly Ser Gln Ile Ile His Asn Ser Gln Lys Pro His Val Val Cys
1               5                   10                  15

Val Pro Tyr Pro Ala Gln Gly His Ile Asn Pro Met Met Arg Val Ala
                20                  25                  30

Lys Leu Leu His Ala Arg Gly Phe Tyr Val Thr Phe Val Asn Thr Val
            35                  40                  45

Tyr Asn His Asn Arg Phe Leu Arg Ser Arg Gly Ser Asn Ala Leu Asp
        50                  55                  60

Gly Leu Pro Ser Phe Arg Phe Glu Ser Ile Ala Asp Gly Leu Pro Glu
65                  70                  75                  80

Thr Asp Met Asp Ala Thr Gln Asp Ile Thr Ala Leu Cys Glu Ser Thr
                85                  90                  95

Met Lys Asn Cys Leu Ala Pro Phe Arg Glu Leu Leu Gln Arg Ile Asn
            100                 105                 110
```

```
Ala Gly Asp Asn Val Pro Pro Val Ser Cys Ile Val Ser Asp Gly Cys
        115                 120                 125

Met Ser Phe Thr Leu Asp Val Ala Glu Glu Leu Gly Val Pro Glu Val
130                 135                 140

Leu Phe Trp Thr Thr Ser Gly Cys Ala Phe Leu Ala Tyr Leu His Phe
145                 150                 155                 160

Tyr Leu Phe Ile Glu Lys Gly Leu Cys Pro Leu Lys Asp Glu Ser Tyr
                165                 170                 175

Leu Thr Lys Glu Tyr Leu Glu Asp Thr Val Ile Asp Phe Ile Pro Thr
            180                 185                 190

Met Lys Asn Val Lys Leu Lys Asp Ile Pro Ser Phe Ile Arg Thr Thr
        195                 200                 205

Asn Pro Asp Asp Val Met Ile Ser Phe Ala Leu Arg Glu Thr Glu Arg
210                 215                 220

Ala Lys Arg Ala Ser Ala Ile Ile Leu Asn Thr Phe Asp Asp Leu Glu
225                 230                 235                 240

His Asp Val Val His Ala Met Gln Ser Ile Leu Pro Pro Val Tyr Ser
                245                 250                 255

Val Gly Pro Leu His Leu Leu Ala Asn Arg Glu Ile Glu Glu Gly Ser
            260                 265                 270

Glu Ile Gly Met Met Ser Ser Asn Leu Trp Lys Glu Glu Met Glu Cys
        275                 280                 285

Leu Asp Trp Leu Asp Thr Lys Thr Gln Asn Ser Val Ile Tyr Ile Asn
290                 295                 300

Phe Gly Ser Ile Thr Val Leu Ser Val Lys Gln Leu Val Glu Phe Ala
305                 310                 315                 320

Trp Gly Leu Ala Gly Ser Gly Lys Glu Phe Leu Trp Val Ile Arg Pro
                325                 330                 335

Asp Leu Val Ala Gly Glu Glu Ala Met Val Pro Pro Asp Phe Leu Met
            340                 345                 350

Glu Thr Lys Asp Arg Ser Met Leu Ala Ser Trp Cys Pro Gln Glu Lys
        355                 360                 365

Val Leu Ser His Pro Ala Ile Gly Gly Phe Leu Thr His Cys Gly Trp
370                 375                 380

Asn Ser Ile Leu Glu Ser Leu Ser Cys Gly Val Pro Met Val Cys Trp
385                 390                 395                 400

Pro Phe Phe Ala Asp Gln Gln Met Asn Cys Lys Phe Cys Cys Asp Glu
                405                 410                 415

Trp Asp Val Gly Ile Glu Ile Gly Gly Asp Val Lys Arg Glu Glu Val
            420                 425                 430

Glu Ala Val Val Arg Glu Leu Met Asp Gly Lys Gly Lys Lys Met
        435                 440                 445

Arg Glu Lys Ala Val Glu Trp Gln Arg Leu Ala Glu Lys Ala Thr Glu
450                 455                 460

His Lys Leu Gly Ser Ser Val Met Asn Phe Glu Thr Val Val Ser Lys
465                 470                 475                 480

Phe Leu Leu Gly Gln Lys Ser Gln Asp
                485

<210> SEQ ID NO 10
<211> LENGTH: 2757
<212> TYPE: DNA
<213> ORGANISM: Arabidopsis thaliana
```

```
<400> SEQUENCE: 10
atgggatctc agatcattca taactcacaa aaaccacatg tagtttgtgt tccatatccg       60
gctcaaggcc acatcaaccc tatgatgaga gtggctaaac tcctccacgc cagaggcttc      120
tacgtcacct tcgtcaacac cgtctacaac cacaatcgtt tccttcgttc tcgtgggtcc      180
aatgccctag atggacttcc ttcgttccga tttgagtcca ttgctgacgg tctaccagag      240
acagacatgg atgccacgca ggacatcaca gctctttgcg agtccaccat gaagaactgt      300
ctcgctccgt tcagagagct tctccagcgg atcaacgctg gagataatgt tcctccggta      360
agctgtattg tatctgacgg ttgtatgagc tttactcttg atgttgcgga ggagcttgga      420
gtcccggagg ttcttttttg gacaaccagt ggctgtgcgt tcctggctta tctacacttt      480
tatctcttca tcgagaaggg cttatgtccg ctaaaaggta cgtattctta cattgattat      540
tgatttaaat gacgttatga tattaaattt aacgtaagaa cccttaagac acctcgagca      600
gggtgagttt ttaatctgag atatatcgtt tgtatattgg ataaaaaata tccatttagc      660
taccatattt agcgaagcca tagactatcc taatcgatcc acccgcacga cgagaccggt      720
caagactcaa gatggtcatg ttgtaatata tactcaattt tatacaattg ttacattgta      780
gcctaggttt ttgagcatta ctaaatatat agtatcaaga gaaatgtcca tattttaata      840
tatacataac gtaatgaatg ttttgatatg ttttttattt cgatgcgttt gcagttttct      900
tgtaatatat atattacagt tttcttagcc aaaaaaaaaa taataatta gagaagatac       960 attgttgatt tattttaaag cattgatatc ttttttaacct tccgcttccc ctatccgctg     1020
gtgaattttg agtgacatta aagattgaac agaaatccca tattttattt tgttaagaga     1080
tgcgtagatt cttaactttg attacagttt aaaatcatgt taaggaaat gatgatgttc      1140 aaaattccat ttcgtatttt acataaattt tgttgttaac ttatcttaaa gttatatgat     1200
atttgcaaac gtcgtctttc tatgattttt attattagtt tgaacgtaaa caaaatatat     1260
ttaatatttg tgaaaaggct tgaaaattgt aaaagaggga tttttaaata gtaacaaatt     1320
ttaggtgaac tatagcgtat ataaaagata ggttatttat ttgtgtaaag attatctgtt     1380
tgtattggtt ccaattttttt tcggtgacct ttaataacat agatgcatca cacatgaaca    1440
tttggtatga aaacaaaaag ataaccaata ttgccaaaaa aaaagaagg agagagacgg      1500 cgggaaagtt tgttgaggaa aaaaataaaa ttgggtaata tccaaacatg aaagtgaaat     1560
aaaccgtaaa aaatcaatgc aatttggcat atcattgtcc agggaccagg ccactctgtc     1620
tttcggtcat attcataact cttttctggct ctgaaattac acaatgaatg ccgtgtccta    1680
gagaatcata tagacgtgga tgcttacgta aatgcataat ttttttctaaa atgcggtgct    1740 tgtattttta ttaactaata tcatgagact tatcttgatt aataaatggt gattgatttg     1800
gcagatgaga gttacttgac gaaggagtac ttagaagaca cggttataga tttttatacca    1860 accatgaaga atgtgaaact aaaggatatt cctagcttca tacgtaccac taatcctgat     1920
gatgttatga ttagtttcgc cctccgcgag accgagcgag ccaaacgtgc ttctgctatc     1980
attctaaaca catttgatga ccttgagcat gatgttgttc atgctatgca atctatctta     2040
cctccggttt attcagttgg accgcttcat ctccttagcaa accgggagat tgaagaaggt    2100
agtgagattg gaatgatgag ttcgaattta tggaaagagg agatggagtg tttggattgg     2160
cttgatacta agactcaaaa tagtgtcatt tatatcaact ttgggagcat aacggttttg     2220
agtgtgaagc agcttgtgga gtttgcttgg ggtttggcgg gaagtgggaa agagttttta    2280
tgggtgatcc ggccagattt agtagcggga gaggaggcta tggttccgcc ggacttttta    2340
```

```
atggagacta aagaccgcag tatgctagcg agttggtgtc ctcaagagaa agtactttct    2400
catcctgcta ttggagggtt tttgacgcat tgcgggtgga actcgatatt ggaaagtctt    2460
tcgtgtggag ttccgatggt gtgttggcca ttttttgctg accagcaaat gaattgtaag    2520 tttttgttgtg acgagtggga tgttgggatt gagataggtg gagatgtgaa gagagaggaa    2580
gttgaggcgg tggttagaga gctcatggat ggagagaagg gaaagaaaat gagagaaaag    2640
gcggtagagt ggcagcgctt agccgagaaa gcgacggaac ataaacttgg ttcttccgtt    2700
atgaattttg agacggttgt tagcaagttt cttttgggac aaaaatcaca ggattaa       2757
```

<210> SEQ ID NO 11
<211> LENGTH: 1470
<212> TYPE: DNA
<213> ORGANISM: Arabidopsis thaliana

<400> SEQUENCE: 11

```
atgggatctc agatcattca taactcacaa aaaccacatg tagtttgtgt tccatatccg      60
gctcaaggcc acatcaaccc tatgatgaga gtggctaaac tcctccacgc cagaggcttc     120
tacgtcacct tcgtcaacac cgtctacaac cacaatcgtt ccttcgttc tcgtgggtcc      180 aatgccctag atggacttcc ttcgttccga tttgagtcca ttgctgacgg tctaccagag     240
acagacatgg atgccacgca ggacatcaca gctctttgcg agtccaccat gaagaactgt     300
ctcgctccgt tcagagagct tctccagcgg atcaacgctg gagataatgt tcctccggta     360
agctgtattg tatctgacgg ttgtatgagc tttactcttg atgttgcgga ggagcttgga     420
gtcccggagg ttctttttg dacaaccagt ggctgtgcgt tcctggctta tctacacttt     480
tatctcttca tcgagaaggg cttatgtccg ctaaaagatg agagttactt gacgaaggag     540
tacttagaag acacggttat agattttata ccaaccatga agaatgtgaa actaaaggat     600
attcctagct tcatacgtac cactaatcct gatgatgtta tgattagttt cgccctccgc     660
gagaccgagc gagccaaacg tgcttctgct atcattctaa acacatttga tgaccttgag     720
catgatgttg ttcatgctat gcaatctatc ttacctccgg tttattcagt tggaccgctt     780
catctcttag caaaccggga gattgaagaa ggtagtgaga ttggaatgat gagttcgaat     840
ttatggaaag aggagatgga gtgtttggat tggcttgata ctaagactca aaatagtgtc     900
atttatatca actttgggag cataacggtt ttgagtgtga agcagcttgt ggagtttgct     960
tggggtttgg cgggaagtgg gaaagagttt ttatgggtga tccggccaga tttagtagcg    1020
ggagaggagg ctatggttcc gccggacttt ttaatggaga ctaaagaccg cagtatgcta    1080
gcgagttggt gtcctcaaga gaaagtactt tctcatcctg ctattggagg ttttttgacg    1140
cattgcgggt ggaactcgat attggaaagt ctttcgtgtg gagttccgat ggtgtgttgg    1200 ccatttttg ctgaccagca aatgaattgt aagttttgtt gtgacgagtg ggatgttggg    1260
attgagatag gtggagatgt gaagagagag gaagttgagg cggtggttag agagctcatg    1320
gatggagaga agggaaagaa aatgagagaa aaggcggtag agtggcagcg cttagccgag    1380
aaagcgacgg aacataaact tggttcttcc gttatgaatt ttgagacggt tgttagcaag    1440
tttcttttgg gacaaaaatc acaggattaa                                     1470
```

<210> SEQ ID NO 12
<211> LENGTH: 31
<212> TYPE: DNA
<213> ORGANISM: Artificial
<220> FEATURE:

```
<223> OTHER INFORMATION: Synthetic DNA

<400> SEQUENCE: 12
cacccatatg ggatctcaga tcattcataa c                              31

<210> SEQ ID NO 13
<211> LENGTH: 33
<212> TYPE: DNA
<213> ORGANISM: Artificial
<220> FEATURE:
<223> OTHER INFORMATION: Synthetic DNA

<400> SEQUENCE: 13
ggatccttaa tcctgtgatt tttgtcccaa aag                            33
```

METHOD FOR UTILIZING MONOTERPENE GLYCOSYLTRANSFERASE

CROSS REFERENCE TO RELATED APPLICATIONS

This application is the National Stage of International Application No. PCT/JP2011/080584, filed Dec. 27, 2011, and claims benefit of Japanese Application No. 2010-293237, filed on Dec. 28, 2010, all of which are herein incorporated by reference in their entirety.

SEQUENCE LISTING

The instant application contains a sequence listing which has been submitted in ASCII format via EFS-Web and is hereby incorporated by reference in its entirety. Said ASCII copy, created on May 15, 2013, is named G13_0018_SEQ_LISTING_ST25.txt and is 35,491 bytes in size.

TECHNICAL FIELD

The present invention relates to a method for producing a monoterpene 8-glycoside, a transformant that highly expresses glycosyltransferase acting on the 8-position of monoterpenes, as well as a monoterpene 8-glycoside produced by the above method and use thereof. The present invention also relates to a plant modified to suppress the expression of a protein having glycosylation activity on the 8-position of a monoterpene compound and use thereof.

BACKGROUND ART

Terpenoids, particularly those with a relatively small molecular weight such as monoterpenes (C10) and sesquiterpenes (C15) serve as major aroma components in plants and are widely used not only as flavors for food products and/or alcoholic beverages, but also even in industrial products including cosmetics and perfumes. It is known that monoterpenes typified by linalool are synthesized within plant cells and are partially accumulated as glycosides. For example, in the case of *Arabidopsis thaliana* of the family Brassicaceae, a glycoside of 8-hydroxylated linalool has been reported (Non-patent Document 1). Not only in model plants, but also in industrially important crops such as *Humulus lupulus* of the family Cannabaceae (Non-patent Document 2), *Camellia sinensis* of the family Theaceae (Non-patent Documents 3 to 6) and *Zingiber officinale* of the family Zingiberaceae (Non-patent Document 7), monoterpene glycosides are known to be accumulated. Further, because of being widely reported in the plant kingdom (Non-patent Document 8), glycosides would be a common form for precursors of aroma components. From the standpoint of industrial application, studies have also been conducted to artificially control the volatilization of aroma components from terpene glycosides serving as aroma precursors through enzymatic or non-enzymatic cleavage of their sugar moieties (Non-patent Document 9).

However, although β-primeverosidase, an enzyme cleaving the sugar moiety from a monoterpene glycoside, has been previously isolated from *Camellia sinensis* (Non-patent Document 10), molecular mechanisms for causing sugar addition (i.e., glycosylation) in monoterpenes have not yet been identified. Based on comprehensive activity screening of UDP-sugar dependent glycosyltransferases (UGTs) in *Arabidopsis thaliana*, some UGT enzymes have been reported to react with monoterpenes in test tubes, but there is no mention of their physiological roles and the significance of their activity (Non-patent Document 11). In *Citrus sinensis* of the family Rutaceae, monoterpene glycosides are also accumulated, and hence attempts have been made to screen UGTs acting on monoterpenes, but such attempts have not succeeded in identifying any active UGT enzyme gene (Non-patent Document 12).

Patent Document 1: WO97/11184
Non-patent Document 1: Aharoni et al (2003) Plant Cell 15, 2866-2884
Non-patent Document 2: Kollmannsberger et al (2006) Mschr. Brauwissenschaft 59, 83-89
Non-patent Document 3: Guo et al (1994) Biosci. Biotech. Biochem. 58, 1532-1534
Non-patent Document 4: Nishikitani et al (1996) Biosci. Biotech. Biochem. 60, 929-931
Non-patent Document 5: Moon et al (1996) Biosci. Biotech. Biochem. 60, 1815-1819
Non-patent Document 6: Ma et al (2001) Phytochemisty 56, 819-825
Non-patent Document 7: Sekiwa et al (1999) Biosci. Biotech. Biochem. 63, 384-389
Non-patent Document 8: Winterhalter and Skouroumounis (1997) Adv. Biochem. Eng. Biotechnol. 55, 73-105
Non-patent Document 9: Herman (2007) Angew. Chem. Int. Ed. 46, 5836-5863
Non-patent Document 10: Mizutani et al (2002) Plant Physiol. 130, 2164-2176
Non-patent Document 11: Caputi et al (2008) Chem. Eur. J. 14, 6656-6662
Non-patent Document 12: Fan et al (2010) Genome 53, 816-823
Non-patent Document 13: Winter et al (2007) PLoS One 2, e718
Non-patent Document 14: Hou et al (2004) J. Biol. Chem. 279, 47822-47832
Non-patent Document 15: Kristensen et al (2005) Proc. Natl. Acd. Sci. USA 102, 1779-1784
Non-patent Document 16: Franks et al (2008) Funct. Plant Biol. 35, 236-246

DISCLOSURE OF THE INVENTION

Under these circumstances, there is a demand for the identification of a UGT enzyme gene and a protein encoded by this gene to establish an efficient method for producing a terpene glycoside by means of such a gene or protein.

As a result of intensive efforts on co-expression analysis in *Arabidopsis thaliana* (ATTED-II), the inventors of the present invention have found, from among 100 or more candidate genes, UGT85A3 and UGT85A1 as UGT enzyme genes showing high expression correlation with the linalool synthase gene (LIS). As a result of further efforts on cloning and detailed characterization of these enzyme genes, the inventors of the present invention have also elucidated that proteins encoded by these genes have glycosylation activity on monoterpenes, and particularly show high specific activity on substrates having a hydroxy group at the 8-position (e.g., 8-hydroxygeraniol and 8-hydroxylinalool). Thus, UGT85A3 and UGT85A1 are in agreement in all of their characteristics, i.e., gene expression pattern, biochemical enzyme function, and the region where their products, i.e., monoterpene glycosides are accumulated, thereby confirming that UGT85A3 and UGT85A1 are both physiological glycosyltransferases acting on linalool. The present invention is based on the above findings.

Namely, the present invention is as follows.

[1] A method for producing a monoterpene 8-glycoside, which comprises the step of reacting a protein of any one selected from the group consisting of (a) to (c) shown below, a UDP-sugar and a monoterpene compound to cause glycosylation at the 8-position of the monoterpene compound:
(a) a protein which consists of the amino acid sequence shown in SEQ ID NO: 2 or 9;
(b) a protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound; and
(c) a protein which has an amino acid sequence sharing a sequence identity of 75% or more with the amino acid sequence shown in SEQ ID NO: 2 or 9 and which has glycosylation activity on the 8-position of a monoterpene compound.

[2] The method according to [1] above, wherein the UDP-sugar is UDP-glucose.

[3] The method according to [1] above, wherein the monoterpene compound is any one selected from the group consisting of 8-hydroxymyrcene, 8-hydroxynerol, 8-hydroxygeraniol and 8-hydroxylinalool.

[4] A non-human transformant transformed with a polynucleotide of any one selected from the group consisting of (a) to (e) shown below:
(a) a polynucleotide containing the nucleotide sequence shown in SEQ ID NO: 1, 3, 8 or 10;
(b) a polynucleotide encoding a protein which consists of the amino acid sequence shown in SEQ ID NO: 2 or 9;
(c) a polynucleotide encoding a protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound;
(d) a polynucleotide encoding a protein which has an amino acid sequence sharing a sequence identity of 75% or more with the amino acid sequence shown in SEQ ID NO: 2 or 9 and which has glycosylation activity on the 8-position of a monoterpene compound; and
(e) a polynucleotide which is hybridizable under high stringent conditions with a polynucleotide consisting of a nucleotide sequence complementary to the nucleotide sequence shown in SEQ ID NO: 1, 3, 8 or 10 and which encodes a protein having glycosylation activity on the 8-position of a monoterpene compound.

[5] The transformant according to [4] above, which contains the nucleotide sequence shown in SEQ ID NO: 1, 3, 8 or 10.

[6] The transformant according to [4] above, wherein the polynucleotide is inserted into an expression vector.

[7] The transformant according to [4] above, which is a plant.

[8] An extract of the transformant according to [4] above.

[9] A food, an aromatic, a pharmaceutical preparation or an industrial raw material, which comprises the extract according to [8] above.

[10] A method for producing a protein having glycosylation activity on the 8-position of a monoterpene compound, which comprises culturing the non-human transformant according to [4] above.

[11] A plant modified to suppress the expression of a protein having glycosylation activity on the 8-position of a monoterpene compound.

[12] The plant according to [11] above, wherein the expression of the protein is suppressed by RNA interference.

[13] A processed product of the plant according to [11] above or a portion of the plant.

[14] An extract of the plant according to [11] above.

[15] A food, an aromatic, a pharmaceutical preparation or an industrial raw material, which comprises the extract according to [14] above.

The method of the present invention allows efficient production of 8-glycosides of terpene compounds. Moreover, the transformants of the present invention are rich in 8-glycosides of terpene compounds, and hence 8-glycosides of terpene compounds can be efficiently extracted and purified from these transformants.

BRIEF DESCRIPTION OF THE DRAWINGS

FIG. 5 shows the chemical information table of monoterpene glycosides.

BEST MODES FOR CARRYING OUT THE INVENTION

Figure 1:
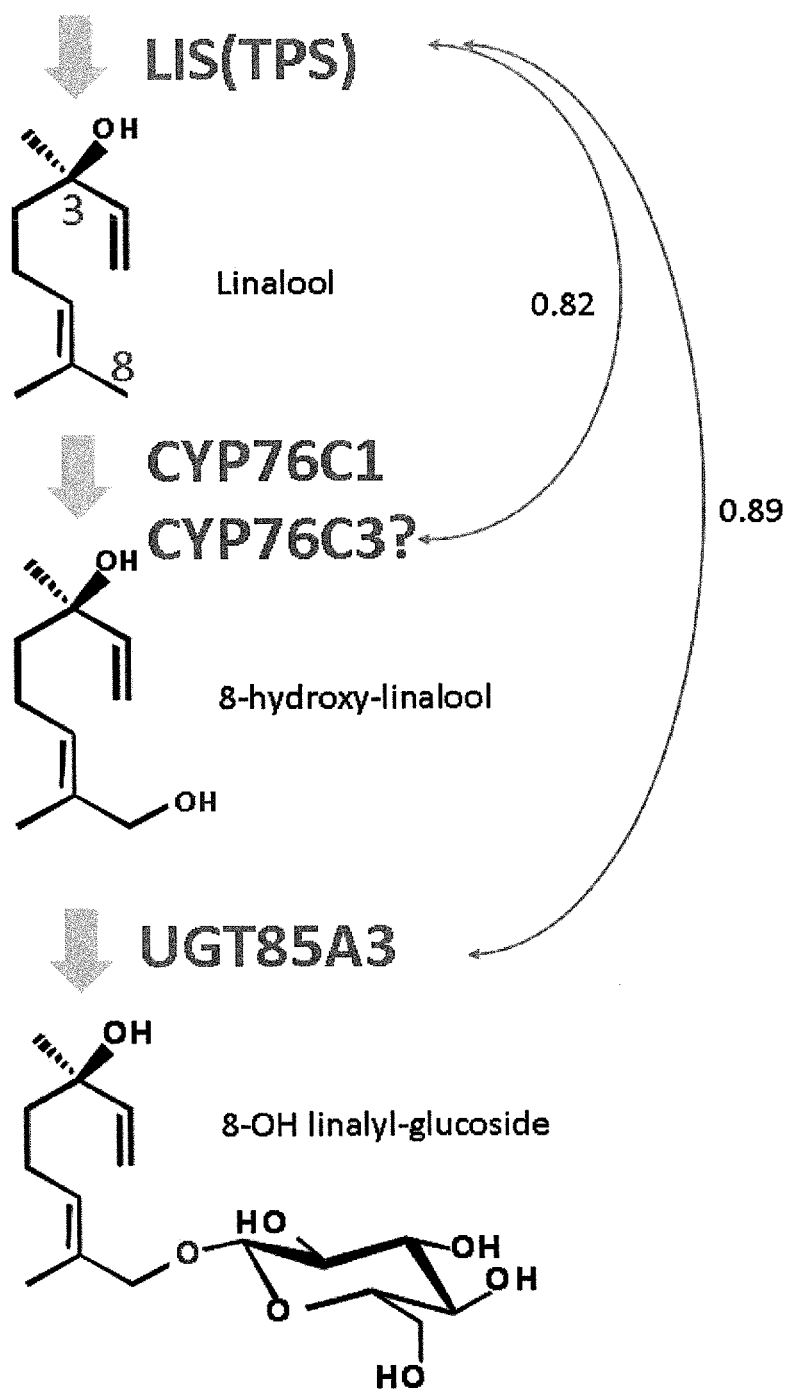
FIG. 1 shows a putative pathway of monoterpene (linalool) metabolism in *Arabidopsis thaliana*. In the figure, the values indicated with arrows each represent a correlation coefficient with ATTED-II.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2010-293237 (filed on Dec. 28, 2010), based on which the present application claims priority.

The inventors of the present invention have elucidated, ahead of others, that enzyme proteins for glycosylation reaction at the 8-position of monoterpene compounds are UGT85A3 and UGT85A1.

The CDS sequence, deduced amino acid sequence, genomic gene sequence, cDNA sequence and open reading frame (ORF) sequence of UGT85A3 are as shown in SEQ ID NOs: 1, 2, 3, 4 and 5, respectively. Likewise, the CDS sequence, deduced amino acid sequence, genomic gene sequence and cDNA sequence of UGT85A1 are as shown in SEQ ID NOs: 8, 9, 10 and 11, respectively. These polynucleotides and enzymes can be obtained by procedures as described later in the Example section, known genetic engineering procedures, known synthesis procedures, etc.

1. Method for Producing a Monoterpene 8-Glycoside

The present invention provides a method for producing a 8-glycoside of a monoterpene compound, which comprises the step of reacting a protein of any one selected from the group consisting of (a) to (c) shown below (hereinafter referred to as "the protein of the present invention"), a UDP-sugar and a monoterpene compound to cause glycosylation at the 8-position of the above monoterpene compound:

(a) a protein which consists of the amino acid sequence shown in SEQ ID NO: 2 or 9;
(b) a protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound; and
(c) a protein which has an amino acid sequence sharing a sequence identity of 75% or more with the amino acid sequence shown in SEQ ID NO: 2 or 9 and which has glycosylation activity on the 8-position of a monoterpene compound.

The above protein (b) or (c) is typically a mutant of the naturally occurring polypeptide shown in SEQ ID NO: 2 or 9, although other examples include those which may be artificially obtained by site-directed mutagenesis as described in "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the expression "protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound" is intended to include proteins which consist of an amino acid sequence with deletion, substitution, insertion and/or addition of, e.g., 1 to 125 amino acid residues, 1 to 120 amino acid residues, 1 to 115 amino acid residues, 1 to 110 amino acid residues, 1 to 105 amino acid residues, 1 to 100 amino acid residues, 1 to 95 amino acid residues, 1 to 90 amino acid residues, 1 to 85 amino acid residues, 1 to 80 amino acid residues, 1 to 75 amino acid residues, 1 to 70 amino acid residues, 1 to 65 amino acid residues, 1 to 60 amino acid residues, 1 to 55 amino acid residues, 1 to 50 amino acid residues, 1 to 49 amino acid residues, 1 to 48 amino acid residues, 1 to 47 amino acid residues, 1 to 46 amino acid residues, 1 to 45 amino acid residues, 1 to 44 amino acid residues, 1 to 43 amino acid residues, 1 to 42 amino acid residues, 1 to 41 amino acid residues, 1 to 40 amino acid residues, 1 to 39 amino acid residues, 1 to 38 amino acid residues, 1 to 37 amino acid residues, 1 to 36 amino acid residues, 1 to 35 amino acid residues, 1 to 34 amino acid residues, 1 to 33 amino acid residues, 1 to 32 amino acid residues, 1 to 31 amino acid residues, 1 to 30 amino acid residues, 1 to 29 amino acid residues, 1 to 28 amino acid residues, 1 to 27 amino acid residues, 1 to 26 amino acid residues, 1 to 25 amino acid residues, 1 to 24 amino acid residues, 1 to 23 amino acid residues, 1 to 22 amino acid residues, 1 to 21 amino acid residues, 1 to 20 amino acid residues, 1 to 19 amino acid residues, 1 to 18 amino acid residues, 1 to 17 amino acid residues, 1 to 16 amino acid residues, 1 to 15 amino acid residues, 1 to 14 amino acid residues, 1 to 13 amino acid residues, 1 to 12 amino acid residues, 1 to 11 amino acid residues, 1 to 10 amino acid residues, 1 to 9 amino acid residues (one or several amino acid residues), 1 to 8 amino acid residues, 1 to 7 amino acid residues, 1 to 6 amino acid residues, 1 to 5 amino acid residues, 1 to 4 amino acid residues, 1 to 3 amino acid residues, 1 to 2 amino acid residues, or a single amino acid residue in the amino acid sequence shown in SEQ ID NO: 2 or 9 and which have glycosylation activity on the 8-position of a monoterpene compound. In general, a smaller number is more preferred for the above deletion, substitution, insertion and/or addition of amino acid residues.

Moreover, examples of such proteins include those which have an amino acid sequence sharing a sequence identity of 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence shown in SEQ ID NO: 2 or 9 and which have glycosylation activity on the 8-position of a monoterpene compound. In general, a larger value is more preferred for the above sequence identity.

In the context of the present invention, the phrase "glycosylation activity on the 8-position of a monoterpene compound" is intended to mean the ability to add a sugar from a UDP-sugar donor to the hydroxy group at the 8-position of a monoterpene compound serving as an aglycon (i.e., glycosylation). The protein of the present invention may also have glycosylation activity on any position other than the 8-position of a monoterpene compound. In this case, the protein of the present invention will cause glycosylation preferentially on the hydroxy group at the 8-position of a monoterpene compound when compared to hydroxy groups at any positions other than the 8-position.

Glycosylation activity on the 8-position of a monoterpene compound can be confirmed as follows: after incubation at a temperature of 20° C. to 40° C. in a neutral buffer of pH 6.0 to 8.0 (e.g., sodium phosphate buffer or potassium phosphate buffer) which contains the protein of the present invention in an amount of 1 to 500 ng (preferably 50 to 200 ng, most preferably 100 ng), a UDP-sugar (e.g., UDP-glucose) at 1 to 1000 µM (preferably 100 to 700 µM, most preferably 500 µM) and a monoterpene compound (e.g., 8-hydroxylinalool) at 1 to 500 μM (preferably 100 to 500 μM, most preferably 250 μM), the above monoterpene is purified and analyzed by known procedures such as liquid chromatography-mass spectrometry (LC-MS), etc.

Likewise, whether or not the protein of the present invention will cause glycosylation preferentially on the hydroxy group at the 8-position of a monoterpene compound when compared to hydroxy groups at any positions other than the 8-position can be confirmed as follows: after the protein of the present invention, a UDP-sugar (e.g., UDP-glucose), a monoterpene compound having a hydroxy group at the 8-position (e.g., 8-hydroxylinalool) and a monoterpene compound having a hydroxy group at any position other than the 8-position (e.g., linalool) are incubated under the same conditions as shown above, the above monoterpenes are each purified and analyzed by known procedures such as LC-MS, etc.

Glycosylation reaction is normally completed within about 1 minute to about 12 hours.

Deletion, substitution, insertion and/or addition of one or several amino acid residues in the amino acid sequence of the protein of the present invention is intended to mean that deletion, substitution, insertion and/or addition of one or several amino acid residues occurs at any one or more positions in the same sequence, and two or more of deletion, substitution, insertion and addition may occur at the same time.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Although the protein of the present invention may be obtained by being expressed from a polynucleotide encoding it (see "the polynucleotide of the present invention" described later) in appropriate host cells, it may also be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

In the context of the present invention, the term "monoterpene compound" refers to a hydrocarbon containing isoprene
Formula 1

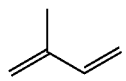

as a constituent unit and encompasses not only biosubstances produced, e.g., by plants, insects and fungi, but also chemically synthesized compounds.

In the present invention, any monoterpene compound can be used as long as it has a hydroxy group at the 8-position (e.g., 8-hydroxymonoterpenoid), and its carbons at positions other than the 8-position may be substituted with any group including a hydroxy group.

Examples of such a monoterpene include, but are not limited to, 8-hydroxymyrcene, 8-hydroxynerol, 8-hydroxygeraniol and 8-hydroxylinalool. Preferred is 8-hydroxygeraniol or 8-hydroxylinalool.

TABLE 1

| 8-Hydroxygeraniol | 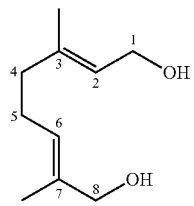 |
| --- | --- |
| 8-Hydroxylinalool | 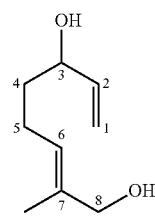 |

In the context of the present invention, the term "UDP-sugar" refers to a uridine diphosphate (UDP)-conjugated sugar, and examples include, but are not limited to, UDP-glucuronic acid and UDP-glucose. A preferred UDP-sugar is UDP-glucose.

The method of the present invention for producing a monoterpene 8-glycoside comprises the step of reacting the protein of the present invention, a UDP-sugar and a monoterpene compound to cause glycosylation at the 8-position of the above monoterpene compound. The method of the present invention may further comprise the step of purifying the 8-glycoside of the monoterpene compound generated in the above step.

The 8-glycoside of the monoterpene compound can be purified by known techniques such as extraction with an appropriate solvent (an aqueous solvent such as water or an organic solvent such as alcohol, ether or acetone), a gradient between an organic solvent (e.g., ethyl acetate) and water, high performance liquid chromatography (HPLC), gas chromatography, time-of-flight mass spectrometry (TOF-MS), ultra (high) performance liquid chromatography (UPLC), etc.

2. Non-Human Transformant Rich in Monoterpene 8-Glycosides

Monoterpene 8-glycosides may also be produced using the protein of the present invention within cells such as those of bacteria (e.g., *E. coli* or yeast), plants, insects, non-human mammals, etc. This is because the protein of the present invention is an enzyme derived from *Arabidopsis thaliana* or a mutant thereof and is therefore expected to have high activity even in the intracellular environment. In this case, a polynucleotide encoding the protein of the present invention (see "the polynucleotide of the present invention" described later) may be introduced into host cells derived from bacteria, plants, insects, non-human mammals or the like to cause expression of the protein of the present invention, followed by reacting the protein of the present invention with UDP-sugars and monoterpene compounds present within the above cells to produce monoterpene 8-glycosides.

Non-human transformants obtained by being transformed with a gene encoding the protein of the present invention are expected to be rich in monoterpene 8-glycosides when compared to their wild-type counterparts.

Then, the present invention provides a non-human transformant transformed with a polynucleotide of any one selected from the group consisting of (a) to (e) shown below (hereinafter referred to as "the polynucleotide of the present invention") (such a transformant is hereinafter referred to as "the transformant of the present invention"):

(a) a polynucleotide containing the nucleotide sequence shown in SEQ ID NO: 1, 3, 8 or 10;
(b) a polynucleotide encoding a protein which consists of the amino acid sequence shown in SEQ ID NO: 2 or 9;
(c) a polynucleotide encoding a protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound;
(d) a polynucleotide encoding a protein which has an amino acid sequence sharing a sequence identity of 75% or more with the amino acid sequence shown in SEQ ID NO: 2 or 9 and which has glycosylation activity on the 8-position of a monoterpene compound; and
(e) a polynucleotide which is hybridizable under high stringent conditions with a polynucleotide consisting of a nucleotide sequence complementary to the nucleotide sequence shown in SEQ ID NO: 1, 3, 8 or 10 and which encodes a protein having glycosylation activity on the 8-position of a monoterpene compound.

As used herein, the term "polynucleotide" is intended to mean DNA or RNA.

As used herein, the expression "polynucleotide which is hybridizable under high stringent conditions" is intended to mean, for example, a polynucleotide that can be obtained by means of colony hybridization, plaque hybridization, Southern hybridization or other hybridization techniques using, as a probe, the whole or a part of a polynucleotide consisting of a nucleotide sequence complementary to the nucleotide sequence shown in SEQ ID NO: 1, 3, 8 or 10 or of a polynucleotide consisting of a nucleotide sequence encoding the amino acid sequence shown in SEQ ID NO: 2 or 9. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "high stringent conditions" refers to, for example, but is not limited to, conditions of 5×SSC, 5×Denhardt's solution, 0.5% SDS, 50% formamide, 50° C. or 0.2×SSC, 0.1% SDS, 60° C., 0.2×SSC, 0.1% SDS, 62° C., 0.2×SSC, 0.1% SDS, 65° C. Under these conditions, it can be expected that DNA having a higher sequence identity is efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to 60° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the nucleotide sequence shown in SEQ ID NO: 1, 3, 8 or 10, or of a nucleotide sequence encoding the amino acid sequence shown in SEQ ID NO: 2 or 9, a DIG nucleic acid detection kit (Roche Diagnostics) may be used for detection of hybridization.

In addition to those listed above, other hybridizable polynucleotides include DNAs sharing a sequence identity of 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA shown in SEQ ID NO: 1, 3, 8 or 10 or with DNA encoding the amino acid sequence shown in SEQ ID NO: 2 or 9, as calculated by homology search software such as FASTA or BLAST using default parameters.

It should be noted that the sequence identity of amino acid sequences or nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, blastp, tblastn and tblastx have been developed (Altschul S F, et al: J Mol Biol 215: 403, 1990). If blastn is used for nucleotide sequence analysis, parameters may be set to, for example, score=100 and wordlength=12. Likewise, if blastp is used for amino acid sequence analysis, parameters may be set to, for example, score=50 and wordlength=3. If BLAST and Gapped BLAST programs are used, default parameters in each program may be used.

The above polynucleotides according to the present invention can be obtained by known genetic engineering procedures or known synthesis procedures.

The polynucleotide of the present invention is preferably introduced into a host in a state of being inserted into an appropriate expression vector.

An appropriate expression vector is generally configured to comprise:
(i) a promoter transcribable in host cells;
(ii) the polynucleotide of the present invention ligated to the promoter; and
(iii) an expression cassette comprising, as constituent elements, signals that function in the host cells for transcription termination and polyadenylation of an RNA molecule.

Such an expression vector may be prepared in any manner, for example, by techniques using plasmids, phages or cosmids, etc.

The actual type of vector is not limited in any way, and any vector expressible in host cells may be selected as appropriate. Namely, a promoter sequence may be selected as appropriate for the type of host cells in order to ensure expression of the polynucleotide of the present invention, and this promoter and the polynucleotide of the present invention may then be integrated into various plasmids or the like for use as expression vectors.

The expression vector of the present invention contains an expression control region(s) (e.g., a promoter, a terminator and/or a replication origin), depending on the type of host into which the expression vector is to be introduced. Promoters for use in bacterial expression vectors may be commonly used promoters (e.g., trc promoter, tac promoter, lac promoter). Likewise, promoters for use in yeast include, for example, glyceraldehyde triphosphate dehydrogenase promoter, PH05 promoter and so on, while promoters for use in filamentous fungi include, for example, amylase, trpC and so on. In addition, examples of promoters used to express a desired gene in plant cells include cauliflower mosaic virus 35S RNA promoter, rd29A gene promoter, rbcS promoter, and mac-1 promoter that is configured to have the enhancer sequence of the above cauliflower mosaic virus 35S RNA promoter at the 5'-side of Agrobacterium-derived mannopine synthase promoter sequence. Examples of promoters for use in animal cell hosts include viral promoters (e.g., SV40 early promoter, SV40 late promoter) and so on.

The expression vector preferably comprises at least one selection marker. For this purpose, auxotrophic markers (ura5, niaD), drug resistance markers (hygromycine, zeocin), geneticin resistance gene (G418r), copper resistance gene (CUP1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991) and so on are available for use.

Although the transformant of the present invention may be prepared (produced) in any manner, an expression vector comprising the polynucleotide of the present invention may be introduced into a host to transform the host, by way of example. Host cells used for this purpose may be of any type, and conventionally known various types of cells can be used preferably. Specific examples include bacteria such as *E. coli*, yeast (budding yeast *Saccharomyces cerevisiae*, fission yeast *Schizosaccharomyces pombe*), plant cells, non-human animal cells and so on.

Culture media and conditions appropriate for the above host cells are well known in the art. Moreover, the organism to be transformed may be of any type, and examples include various types of microorganisms or plants or non-human animals as listed above for host cells.

For transformation of host cells, commonly used known techniques can be used. For example, transformation may be accomplished by, but is not limited to, electroporation (Mackenxie, D. A. et al., Appl. Environ. Microbiol., vol. 66, p. 4655-4661, 2000), particle delivery method (described in JP 2005-287403 A entitled "Breeding Method of Lipid Producing Fungi"), spheroplast method (Proc. Natl. Acad. Sci. USA, vol. 75, p. 1929, 1978), lithium acetate method (J. Bacteriology, vol. 153, p. 163, 1983), and other methods as described in Methods in yeast genetics, 2000 Edition: A Cold Spring Harbor Laboratory Course Manual.

In addition, as for standard molecular biological procedures, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

In one embodiment of the present invention, the transformant may be a plant transformant. The plant transformant according to this embodiment may be obtained by introducing a recombinant vector comprising the polynucleotide of the present invention into a plant such that a polypeptide encoded by this polynucleotide can be expressed.

In cases where a recombinant expression vector is used, any recombinant expression vector may be used for transformation of a whole plant as long as it is a vector allowing the polynucleotide of the present invention to be expressed within the plant. Examples of such a vector include those having a promoter which drives constitutive expression of a desired polynucleotide within plant cells or those having a promoter whose activation is induced by external stimulation.

Examples of a promoter which drives constitutive expression of a desired polynucleotide within plant cells include cauliflower mosaic virus 35S RNA promoter, rd29A gene promoter, rbcS promoter, mac-1 promoter, etc.

Examples of a promoter whose activation is induced by external stimulation include mouse mammary tumor virus (MMTV) promoter, tetracycline-responsive promoter, metallothionein promoter and heat shock protein promoter, etc.

The plant to be transformed in the present invention is intended to mean any of a whole plant, a plant organ (e.g., leaf, petal, stem, root, seed), a plant tissue (e.g., epidermis, phloem, parenchyma, xylem, vascular bundle, palisade tissue, spongy parenchyma) or a plant cultured cell, or alternatively, various forms of plant cells (e.g., suspension cultured cells), a protoplast, a leaf section, a callus and so on. The plant used for transformation may be of any type, belonging to either monocotyledons or dicotyledons.

For gene transfer into plants, transformation techniques known to those skilled in the art may be used (e.g., *Agrobacterium*-mediated method, gene gun method, PEG-mediated method, electroporation). For example, *Agrobacterium*-mediated method and direct gene transfer into plant cells are well known. In the case of using the *Agrobacterium*-mediated method, the constructed plant expression vector may be introduced into an appropriate *Agrobacterium* strain (e.g., *Agrobacterium tumefaciens*) and this strain may then be infected into a leaf section cultured under sterile conditions, e.g., in accordance with the leaf disk method (Hirofumi Miyauchi, Manuals for Plant Genetic Engineering (1990) pages 27-31, Kodansha Scientific Ltd., Tokyo) to thereby obtain a transgenic plant. Alternatively, it is possible to use the method of Nagel et al. (Micribiol. Lett., 67: 325 (1990)). In this method, for example, an expression vector is first introduced into *Agrobacterium*, and the transformed *Agrobacterium* is then introduced into plant cells or plant tissues as described in Plant Molecular Biology Manual (Gelvin, S. B. et al., Academic Press Publishers). As used herein, the term "plant tissue" also includes a callus obtainable by culturing plant cells. In cases where the *Agrobacterium*-mediated method is used for transformation, a binary vector (e.g., pBI121 or pPZP202) may be used.

Likewise, techniques known for direct gene transfer into plant cells or plant tissues are electroporation and particle gun method. In the case of using a particle gun, a whole plant, a plant organ or a plant tissue may be used directly, or sections may be prepared therefrom before use, or protoplasts may be prepared and used. The thus prepared samples may be treated using a gene transfer device (e.g., PDS-1000 (BIO-RAD)). Although treatment conditions will vary depending on the type of plant or sample, the treatment is generally conducted at a pressure of about 450 to 2000 psi and at a distance of about 4 to 12 cm.

The transformed cells or plant tissues are first selected by drug resistance such as hygromycin resistance, and then regenerated into whole plants in a standard manner. Regeneration from transformed cells into whole plants may be accomplished by techniques known to those skilled in the art as appropriate for the type of plant cells.

In cases where cultured plant cells are used as a host, transformation may be accomplished by introducing a recombinant vector into the cultured cells with a gene gun or by electroporation, etc. Calli, shoots, hairy roots and the like obtained as a result of transformation may be used directly for cell culture, tissue culture or organ culture, and may also be regenerated into whole plants using conventionally known procedures for plant tissue culture, e.g., by being administered with an appropriate concentration of a plant hormone (e.g., auxin, cytokinin, gibberellin, abscisic acid, ethylene, brassinolide).

Confirmation of whether or not the polynucleotide of the present invention has been introduced into a plant may be accomplished by PCR, Southern hybridization, Northern hybridization, etc. For example, DNA is prepared from a transgenic plant and DNA specific primers are designed for PCR. PCR may be performed under the same conditions as used for preparation of the above plasmid. Then, amplification products may be subjected to, e.g., agarose gel electrophoresis, polyacrylamide gel electrophoresis or capillary electrophoresis, followed by staining with ethidium bromide, SYBR Green solution, etc. If the amplification products are detected as a single band, it can be confirmed that the plant has been transformed. Alternatively, primers which have been labeled with a fluorescent dye or the like may be used in PCR to thereby detect amplification products. Further, it is also possible to use techniques in which amplification products are bound onto a solid phase (e.g., a microplate) and confirmed by fluorescence or enzymatic reaction, etc.

Once a transgenic whole plant whose genome carries the polynucleotide of the present invention has been obtained, progeny plants may be obtained by sexual or asexual reproduction of the whole plant. Moreover, from such a whole plant or progeny plants thereof or clones thereof, for example, seeds, fruits, cuttings, tubers, root tubers, rootstocks, calli, protoplasts or the like may be obtained and used to achieve mass production of the whole plant. Thus, the present invention also encompasses a whole plant into which the polynucleotide of the present invention has been introduced in an expressible form, or progeny plants of the whole plant which have the same properties as the whole plant, or tissues derived from the whole plant and progeny plants thereof.

In addition, transformation techniques for various plants have already been reported. Transgenic plants according to the present invention include plants of the family Solanaceae (e.g., eggplant, tomato, hot pepper, potato, tobacco, stramonium, Chinese lantern plant, petunia, calibrachoa, nierembergia), plants of the family Leguminosae (e.g., soybean, adzuki bean, peanut, kidney bean, broad bean, Bird's foot trefoil), plants of the family Rosaceae (e.g., strawberry, Japanese apricot, cherry tree, rose, blueberry, blackberry, bilberry, cassis, raspberry), plants of the family Caryophyllaceae (e.g., carnation, gypsophila), plants of the family Asteraceae (e.g., chrysanthemum, gerbera, sunflower, daisy), plants of the family Orchidaceae (e.g., orchid), plants of the family Primulaceae (e.g., cyclamen), plants of the family Gentianaceae (e.g., showy prairie gentian, gentian), plants of the family Iridaceae (e.g., freesia, iris, gladiolus), plants of the family Scrophulariaceae (e.g., snapdragon, torenia), stone crop (kalanchoe), plants of the family Liliaceae (e.g., lily, tulip), plants of the family Convolvulaceae (e.g., morning glory, ivy-leaved morning glory, moonflower, sweet potato, cypress vine, evolvulus), plants of the family Hydrangeaceae (e.g., hydrangea, deutzia), plants of the family Cucurbitaceae (e.g., bottle gourd), plants of the family Geraniaceae (e.g., pelargonium, geranium), plants of the family Oleaceae (e.g., weeping forsythia), plants of the family Vitaceae (e.g., grape), plants of the family Theaceae (e.g., camellia, tea plant), plants of the family Gramineae (e.g., rice, barley, wheat, oat, rye, maize, foxtail millet, Japanese barnyard millet, kaoliang, sugar cane, bamboo, wild oat, finger millet, sorghum, Manchurian wild rice, job's tears, pasture grass), plants of the family Moraceae (e.g., mulberry, hop, paper mulberry, rubber tree, cannabis), plants of the family Rubiaceae (e.g., coffee tree, gardenia), plants of the family Fagaceae (e.g., oak, beech, Japanese emperor oak), plants of the family Pedaliaceae (e.g., sesame), plants of the family Rutaceae (e.g., bitter orange, Citrus junos, satsuma mandarin, Japanese pepper tree), plants of the family Brassicaceae (e.g., red cabbage, flowering cabbage, Japanese radish, white shepherd's purse, Chinese colza, cabbage, broccoli, cauliflower), and plants of the family Lamiacea (e.g., salvia, perilla, lavender, skullcap). Examples of preferred plants include aromatic plants (e.g., perilla and lavender), as well as garden plants (e.g., carnation) which are inherently less aromatic but are of high commercial value.

The whole plant transformed with the polynucleotide of the present invention (hereinafter referred to as "the plant of the present invention" or "the whole plant of the present invention") is rich in 8-glycosides of monoterpene compounds when compared to the wild-type counterpart.

The plant of the present invention can be easily obtained as a perfect whole plant by being grown from a seed, a cuttage, a bulb or the like of the plant of the present invention.

Thus, the plant of the present invention encompasses a whole plant, a plant organ (e.g., leaf, petal, stem, root, seed, bulb), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on.

3. Extract of Transformant and Use Thereof.

In another embodiment, the present invention also provides an extract of the above transformant. Since the transformant of the present invention is rich in monoterpene 8-glycosides when compared to the wild-type counterpart, an extract of the transformant is considered to contain monoterpene 8-glycosides at high concentrations.

Such an extract of the transformant of the present invention can be obtained as follows: the transformant is homogenized with, e.g., glass beads, a homogenizer or a sonicator and the resulting homogenate is centrifuged to collect the supernatant. In addition, a further extraction step may also be provided in accordance with extraction procedures for monoterpene 8-glycosides as mentioned above.

The extract of the transformant of the present invention can be provided for use in, e.g., production of foods, aromatics, pharmaceutical preparations and/or industrial raw materials (e.g., raw materials for cosmetics, soaps, etc.) according to standard practice.

In another embodiment, the present invention also provides a food, an aromatic, a pharmaceutical preparation and/or an industrial raw material (e.g., raw materials for cosmetics, soaps, etc.), each containing the extract of the transformant of the present invention. Such a food, an aromatic, a pharmaceutical preparation and/or an industrial raw material, each containing the extract of the transformant of the present invention, may be prepared in a routine manner. In this way, such a food, an aromatic, a pharmaceutical preparation and/or an industrial raw material, each containing the extract of the transformant of the present invention, contains monoterpene 8-glycosides generated by using the transformant of the present invention.

The aromatic (composition) or pharmaceutical preparation (composition) of the present invention may be in any dosage form, such as solution, paste, gel, solid, powder and other dosage forms. Moreover, the aromatic composition or pharmaceutical composition of the present invention may be used in cosmetics or external preparations for skin (e.g., oil, lotion, cream, emulsion, gel, shampoo, hair conditioner, nail enamel, foundation, lipstick, face powder, facial pack, ointment, perfume, powder, eau de cologne, dentifrice, soap, aerosol, cleansing foam), as well as bath preparations, hair growth promoters, skin essences, sunscreening agents and so on.

When required, the cosmetic composition of the present invention may further be blended as appropriate with additional ingredients such as fats or oils, and/or dyes, aromatics, antiseptics, surfactants, pigments, antioxidants, etc. The blending ratio of these ingredients may be determined by those skilled in the art as appropriate for the intended purpose (e.g., fats or oils may be contained in the composition at a ratio of 1% to 99.99% by weight, preferably 5% to 99.99% by weight, more preferably 10% to 99.95% by weight). Likewise, the pharmaceutical composition of the present invention may further comprise additional pharmaceutically active ingredients (e.g., anti-inflammatory ingredient) or auxiliary ingredients (e.g., lubricating ingredient, carrier ingredient), when required.

Examples of the food of the present invention include nutritional supplementary foods, health foods, functional foods, children's foods, geriatric foods and so on. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods.

These foods and food products may be in the form of agricultural foods including bakery products, noodles, cooked rice, sweets (e.g., candies, chewing gums, gummies, tablets, Japanese sweets), bean curd and processed products thereof; fermented foods including Japanese rice wine (sake), medicinal liquor, sweet cooking sherry (mirin), vinegar, soy sauce and miso (bean paste); livestock food products including yogurt, ham, bacon and sausage; seafood products including fish cake (kamaboko), deep-fried fish cake (ageten) and puffy fish cake (hanpen); as well as fruit drinks, soft drinks, sports drinks, alcoholic beverages, tea or flavor enhancers.

4. Plant Modified to Suppress the Expression of Glycosyltransferase Acting on the 8-Position of Monoterpenes When suppressing the expression of a protein endogenously occurring in plants and having glycosylation activity on the 8-position of monoterpene compounds, monoterpenes are inhibited from being glycosylated. As a result, such a plant will contain more monoterpenes in the form of aglycon and can be expected to release a stronger aroma.

The present invention therefore provides a plant modified to suppress the expression of a protein having glycosylation activity on the 8-position of monoterpene compounds.

More specifically, such a protein having glycosylation activity on the 8-position of monoterpene compounds (hereinafter referred to as "glycosyltransferase acting on the 8-position of monoterpenes") is encoded by a polynucleotide of any one selected from the group consisting of (a) to (e) shown below:

(a) a polynucleotide containing the nucleotide sequence shown in SEQ ID NO: 1, 3, 8 or 10;
(b) a polynucleotide encoding a protein which consists of the amino acid sequence shown in SEQ ID NO: 2 or 9;
(c) a polynucleotide encoding a protein which consists of an amino acid sequence with deletion, substitution, insertion and/or addition of 1 to 125 amino acids in the amino acid sequence shown in SEQ ID NO: 2 or 9 and which has glycosylation activity on the 8-position of a monoterpene compound;
(d) a polynucleotide encoding a protein which has an amino acid sequence sharing a sequence identity of 75% or more with the amino acid sequence shown in SEQ ID NO: 2 or 9 and which has glycosylation activity on the 8-position of a monoterpene compound; and
(e) a polynucleotide which is hybridizable under high stringent conditions with a polynucleotide consisting of a nucleotide sequence complementary to the nucleotide sequence shown in SEQ ID NO: 1, 3, 8 or 10 and which encodes a protein having glycosylation activity on the 8-position of a monoterpene compound.

The polynucleotides (a) to (e) are as defined above in "2. Non-human transformant rich in monoterpene 8-glycosides."

Specific examples of means to suppress the expression of glycosyltransferase acting on the 8-position of monoterpenes include substances capable of reducing the expression level of messenger RNA (mRNA) for this enzyme, as exemplified by low molecular compounds, hormones, proteins and nucleic acids. In one embodiment, such a substance may be a nucleic acid capable of suppressing the functions or expression of a gene encoding the above enzyme. Examples of such a nucleic acid include hairpin-shaped shRNAs (short hairpin RNAs) or double-stranded RNAs (dsRNAs) which produce siRNAs (small interfering RNAs) for RNA interference (RNAi), as well as antisense nucleic acids, decoy nucleic acids, or aptamers, etc. These inhibitory nucleic acids are able to suppress the expression of the above gene. The target gene to be inhibited which encodes glycosyltransferase acting on the 8-position of monoterpenes consists of any one of the above polynucleotides (a) to (e), and sequence information can be obtained for each polynucleotide. In the present invention, it is possible to use, as a target region to be inhibited, not only a coding region, but also a non-coding region of the gene encoding glycosyltransferase acting on the 8-position of monoterpenes.

RNA interference (RNAi) is a multi-step process proceeding through a number of stages. First of all, dsRNA or shRNA expressed from an RNAi expression vector is recognized by Dicer and cleaved into siRNAs of 21 to 23 nucleotides. These siRNAs are then integrated into an RNAi targeting complex, which is called the RNA-induced silencing complex (RISC), and the complexes between RISC and siRNAs bind to target mRNA containing sequences complementary to the siRNA sequences and thereby cleave the mRNA. The target mRNA is cleaved in the center of its region complementary to the siRNA, finally leading to rapid degradation of the target mRNA and reduced protein expression levels. The most potent siRNA duplexes are known to be sequences of 21 nucleotides in length, each comprising a 19 bp duplex with an overhang of two uridine residues at the 3'-terminal end (Elbashir S. M. et al., Genes and Dev, 15, 188-200 (2001)).

In general, a target sequence on mRNA may be selected from the cDNA sequence corresponding to the mRNA. However, the present invention is not limited to this region.

siRNA molecules may be designed on the basis of the criteria well known in the art. For example, as a target segment in target mRNA, it is possible to select a segment covering 15 to 30 contiguous bases, preferably 19 to 25 contiguous bases, preferably starting with AA, TA, GA or CA. siRNA molecules have a GC ratio of 30% to 70%, preferably 35% to 55%. Alternatively, a target sequence for RNAi may be selected as appropriate as described in Ui-Tei K. et al. ((2004) Nucleic Acids Res. 32, 936-948).

For introduction of siRNA into cells, it is possible to use, e.g., procedures in which synthesized siRNA is ligated to plasmid DNA and then introduced into cells, or procedures in which double-stranded RNA is annealed.

In the present invention, shRNA may also be used for providing RNAi effect. shRNA is an RNA molecule called short hairpin RNA, which has a stem-loop structure because some single-stranded regions form complementary strands with other regions.

shRNA may be designed to form a stem-loop structure as a part thereof. For example, assuming that a sequence covering a certain region is designated as sequence A, and a strand complementary to the sequence A is designated as sequence B, shRNA is designed to comprise the sequence A, a spacer and the sequence B linked in this order on a single RNA strand and to have an overall length of 45 to 60 bases. The spacer may also have any length.

Although the sequence A is a sequence covering a partial region of the target gene encoding glycosyltransferase acting on the 8-position of monoterpenes, there is no particular limitation on the target region and any region may be selected as a candidate for the target region. In addition, the sequence A has a length of 19 to 25 bases, preferably 19 to 21 bases.

Further, in the present invention, microRNA may be used to inhibit the expression of glycosyltransferase acting on the 8-position of monoterpenes. microRNA (miRNA) is an intracellular single-stranded RNA molecule having a length of about 20 to 25 bases and is a kind of ncRNA (non-coding RNA) which is considered to have the function of regulating the expression of other genes. miRNA is generated through processing upon transcription into RNA and is present as a nucleic acid capable of forming a hairpin structure which suppresses the expression of a target sequence.

Since miRNA is also an inhibitory nucleic acid based on RNAi, miRNA may also be designed and synthesized in the same manner as in the case of shRNA or siRNA.

Expression vectors for RNAi may be readily prepared with a commercially available DNA/RNA synthesizer (e.g., Applied Biosystems model 394) on the basis of pMuniH1 plasmid, pSINsi vector (Takara Bio Inc., Japan), pSIF1-H1 (System Biosciences, Inc.), etc. Examples of expression vectors for RNAi include, but are not limited to, pSPB1876 (WO2004/071467). Expression vectors for RNAi may be prepared by entrusting their preparation to third parties such as Cosmo Bio Co., Ltd. (Japan), Takara Bio Inc. (Japan), Invitrogen, Promega, etc.

A method for producing a plant modified to suppress the expression of glycosyltransferase acting on the 8-position of monoterpenes may comprise the following steps.

(1) Step of Introducing an Expression Vector for RNAi (e.g., siRNA Expression Vector or miRNA Expression Vector) Against Glycosyltransferase Acting on the 8-Position of Monoterpenes into a Host Plant or a Portion Thereof Introduction of an expression vector for RNAi into a host plant may be accomplished in the same manner as described above in the section "2. Non-human transformant rich in monoterpene 8-glycosides." The host plant may be any of a whole plant or a portion thereof, i.e., a plant organ (e.g., leaf, petal, stem, root, seed), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on. The type of plant is also as described above in the section "2. Non-human transformant rich in monoterpene 8-glycosides."

(2) Step of Growing the Transgenic Plant Obtained in the Above Step (1)

If the host plant used in the above step (1) is a portion of a whole plant, such as a plant organ, a plant tissue, a plant cell, a protoplast, a leaf section or a callus, the resulting transformant may be grown in an appropriate environment until a perfect whole plant is formed. With respect to techniques for growing a portion of a whole plant into a perfect whole plant, reference may be made to the descriptions in the following document: Biochemistry Experiments Vol. 41, An Introduction to Plant Cell Technology, Japan Scientific Societies Press, ISBN 4-7622-1899-5.

Upon cultivation of the thus obtained plant which is modified to suppress the expression of the gene encoding glycosyltransferase acting on the 8-position of monoterpenes, monoterpene aglycons can be produced efficiently.

5. Processed Product of a Plant Modified to Suppress the Expression of the Gene Encoding Glycosyltransferase Acting on the 8-Position of Monoterpenes Today, not only natural flowers (e.g., soil-grown plants, potted plants, cut flowers), but also processed products of natural flowers are sold as products for plant appreciation. Due to their strong aroma, plants modified to suppress the expression of the gene encoding glycosyltransferase acting on the 8-position of monoterpenes are also very useful as materials for such processed products of natural flowers. Thus, another embodiment of the present invention is a processed product of a plant (e.g., natural flower, cut flower) modified to suppress the expression of the gene encoding glycosyltransferase acting on the 8-position of monoterpenes or a portion of the plant (e.g., leaf, petal, stem, root, seeds, bulb). Examples of such a processed product include, but are not limited to, pressed flowers, dried flowers, preserved flowers, material flowers, resin-embedded products, etc.

6. Extract of a Plant Modified to Suppress the Expression of Glycosyltransferase Acting on the 8-Position of Monoterpenes and Use Thereof.

In another embodiment, the present invention also provides an extract of the above plant modified to suppress the expression of glycosyltransferase acting on the 8-position of monoterpenes. Since the plant modified to suppress the expression of glycosyltransferase acting on the 8-position of monoterpenes is rich in monoterpene aglycons when compared to the wild-type counterpart, an extract of the modified plant is considered to contain monoterpene aglycons at high concentrations.

The above extract can be extracted in the same manner as described above for the extract of the transformant of the present invention.

The thus obtained extract can be provided for use in, e.g., production of foods, aromatics, pharmaceutical preparations and/or industrial raw materials (e.g., raw materials for cosmetics, soaps, etc.) according to standard practice.

In another embodiment, the present invention also provides a food, an aromatic, a pharmaceutical preparation and/or an industrial raw material (e.g., raw materials for cosmetics, soaps, etc.), each containing the above extract. Such a food, an aromatic, a pharmaceutical preparation and/or an industrial raw material, each containing the above extract, may be prepared in a routine manner. In this way, such a food, an aromatic, a pharmaceutical preparation and/or an industrial raw material, each containing the extract of the plant modified to suppress the expression of glycosyltransferase acting on the 8-position of monoterpenes, contain monoterpene aglycons generated by using the plant modified to suppress the expression of glycosyltransferase acting on the 8-position of monoterpenes.

The food, aromatic, pharmaceutical preparation and industrial raw material of the present invention are of the same type and composition as described above in the section "3. Extract of transformant and use thereof."

7. Screening Method for a Plant Rich in Terpene 8-Glycosides or a Plant Rich in Monoterpene Aglycons The present invention provides a screening method for a plant rich in monoterpene aglycons. More specifically, the above method comprises steps (1) to (3) shown below:
(1) the step of extracting mRNA from a test plant;
(2) the step of allowing hybridization between the above mRNA or cDNA prepared from the above mRNA and a polynucleotide which is hybridizable under high stringent conditions with a polynucleotide consisting of a nucleotide sequence complementary to the polynucleotide of the present invention; and
(3) the step of detecting the above hybridization.

The above step (1) may be accomplished by extracting mRNA from a test plant. Although mRNA may be extracted from any site of the test plant, preferred are petals. Once mRNA has been extracted, cDNA may be prepared from the mRNA through reverse transcription.

The above step (2) may be accomplished as follows: a polynucleotide or oligonucleotide consisting of a nucleotide sequence complementary to the polynucleotide of the present invention is used as a probe or primer and allowed to hybridize with the mRNA extracted above under high stringent conditions. High stringent conditions are as already described above. Such a polynucleotide or oligonucleotide has a length of preferably 5 to 500 bp, more preferably 10 to 200 bp, and even more preferably 10 to 100 bp. The polynucleotide or oligonucleotide may be readily synthesized with various automatic synthesizers (e.g., AKTA oligopilot plus 10/100 (GE Healthcare)), or alternatively, its synthesis may be entrusted to a third party (e.g., Promega or Takara), etc.

When the polynucleotide consisting of a nucleotide sequence complementary to the polynucleotide of the present invention is used as a probe in the step (2), the step (3) may be accomplished by commonly used techniques for detection of hybridization, such as Southern blotting, Northern blotting (Sambrook, Fritsch and Maniatis, "Molecular Cloning: A Laboratory Manual" 2nd Edition (1989), Cold Spring Harbor Laboratory Press), microarrays (Affymetrix; see U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), or fluorescent in situ hybridization (FISH) (Sieben V. J. et al., (2007-06). IET Nanobiotechnology 1 (3): 27-35). On the other hand, when the polynucleotide consisting of a nucleotide sequence complementary to the polynucleotide of the present invention is used as a primer in the step (2), the step (3) may be accomplished by PCR amplification and the subsequent analysis of the resulting amplification products by electrophoresis or sequencing (Sambrook, Fritsch and Maniatis, "Molecular Cloning: A Laboratory Manual" 2nd Edition (1989), Cold Spring Harbor Laboratory Press), etc., to detect hybridization.

A whole plant in which hybridization was more often detected can be regarded as expressing higher levels of a protein having glycosylation activity on the 8-position of a monoterpene compound than other whole plants, and hence such a whole plant is predicted to be rich in terpene 8-glycosides.

On the other hand, a whole plant in which hybridization was less often detected shows lower expression of a protein having glycosylation activity on the 8-position of a monoterpene compound than other whole plants, and hence such a whole plant is predicted to be rich in monoterpene aglycons, and in particular to release a strong aroma during flowering.

EXAMPLES

The present invention will now be described in more detail by way of the following examples, which are not intended to limit the scope of the present invention.

Example 1

Isolation of Candidate Genes

The molecular biological procedures used in this example were in accordance with the methods described in Molecular Cloning (Sambrook, et al., Cold Spring Harbour Laboratory Press, 2001), unless detailed elsewhere.

Figure 2:
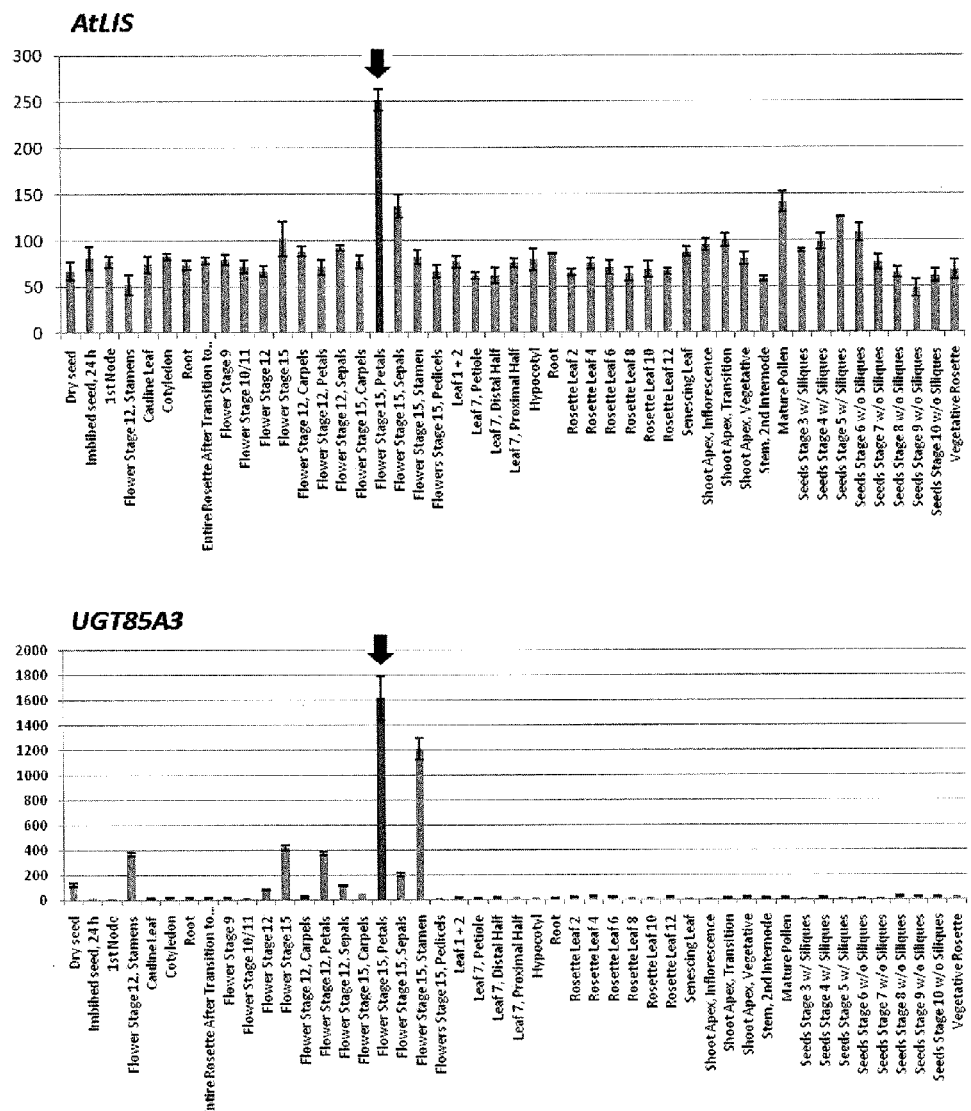
FIG. 2 shows the gene expression profiles of AtLIS and UGT85A3 in different organs. The arrows in the figure each indicate expression in petals.
Figure 3:
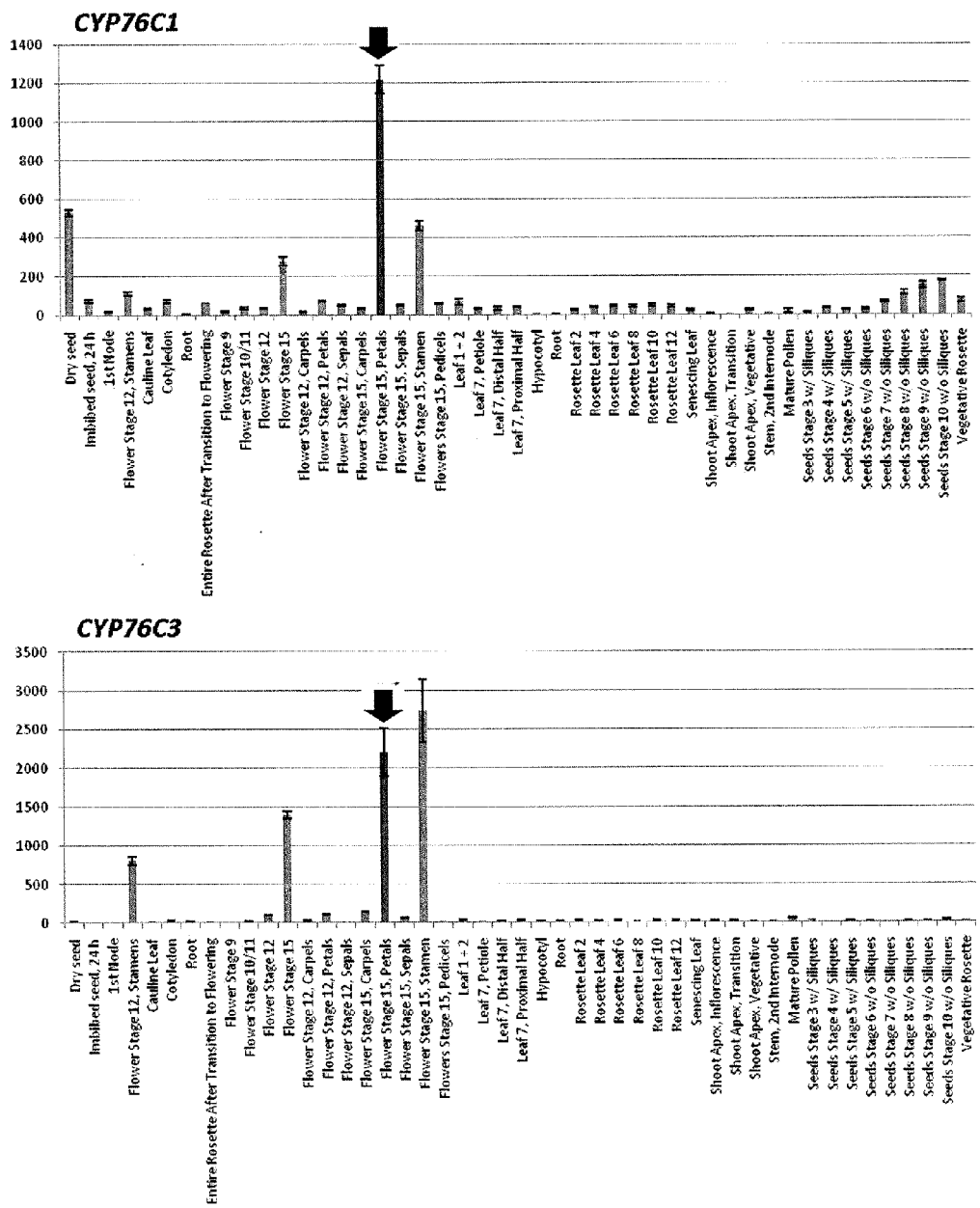
FIG. 3 shows the gene expression profiles of CYP76C1 and CYP76C3. The arrows in the figure each indicate expression in petals.

*Arabidopsis thaliana* is reported to show accumulation of a compound having glucose added to the hydroxyl group at the 8-position of linalool, a kind of monoterpene (FIG. 1) (Non-patent Document 1). Based on the hypothesis that synthesis of linalool and glycosylation of linalool occur in a synchronized manner in terms of the time and space, a gene to be co-expressed with linalool synthase (S-linalool synthase (LIS): At1g69680) in *Arabidopsis thaliana* was examined by ATTED-II co-expression analysis (http://prime.psc.riken.jp/?action=coexpression_index). As a result, from among one hundred and several tens of candidate genes, UGT85A3 (At1g22380) was found as a candidate UGT gene showing high correlation with linalool synthase at an expression coefficient as high as 0.89. These two genes were visualized with eFP Browser (http://bbc.botany.utoronto.ca/efp/cgi-bin/efpWeb.cgi) (Non-patent Document 13), indicating that both genes were strongly expressed particularly in flowers (FIG. 2). CYP76C1, a cytochrome P450 enzyme known as an enzyme introducing a hydroxyl group at the 8-position of linalool, and its homolog CYP76C3 were also found to be strongly expressed in petals (FIG. 3) (Patent Document 1). CYP76C3 showed a strong expression correlation as high as 0.82 with the LIS gene. The above results strongly suggested that UGT85A3 would play a cooperative role with LIS and CYP76C1/C3 primarily in petal cells.

Example 2

Construction of UGT85A3 Expression Vector

The full-length ORF (SEQ ID NO: 5) of UGT85A3 was amplified by PCR with the following primers designed to have restriction enzyme sites (SEQ ID NOs: 6 and 7). It should be noted that the underlined nucleotide sequences in the primers are restriction enzyme recognition sequences added to the primers.

UGT85A3 cDNA (At1g22380):

(SEQ ID NO: 5)
ATGGGATCCCGTTTTGTTTCTAACGAACAAAAACCACACGTAGTTTGCG

TGCCTTACCCAGCTCAAGGCCACATTAACCCTATGATGAAAGTGGCTAA

ACTCCTCCACGTCAAAGGCTTCCACGTCACCTTCGTCAACACCGTCTAC

AACCACAACCGTCTACTCCGATCCCGTGGGGCCAACGCACTCGATGGAC

TTCCTTCCTTCCAGTTCGAGTCAATACCTGACGGTCTTCCGGAGACTGG

CGTGGACGCCACGCAGGACATCCCTGCCCTTTCCGAGTCCACAACGAAA

AACTGTCTCGTTCCGTTCAAGAAGCTTCTCCAGCGGATTGTCACGAGAG

AGGATGTCCCTCCGGTGAGCTGTATTGTATCAGATGGTTCGATGAGCTT

TACTCTTGACGTAGCGGAAGAGCTTGGTGTTCCGGAGATTCATTTTGG

ACCACTAGTGCTTGTGGCTTCATGGCTTATCTACACTTTTATCTCTTCA

TCGAGAAGGGTTTATGTCCAGTAAAAGATGCGAGTTGCTTGACGAAGAG

ATACTTGGACACAGTTATAGATTGGATACCGTCAATGAACAATGTAAAA

CTAAAAGACATTCCTAGTTTTATACGTACCACTAATCCTAACGACATAA

TGCTCAACTTCGTTGTCCGTGAGGCATGTCGAACCAAACGTGCCTCTGC

TATCATTCTGAACACGTTTGATGACCTTGAACATGACATAATCCAGTCT

ATGCAATCCATTTTACCACCGGTTTATCCAATCGGACCGCTTCATCTCT

TAGTAAACAGGGAGATTGAAGAAGATAGTGAGATTGGAAGGATGGGATC

AAATCTATGGAAAGAGGAGACTGAGTGCTTGGGATGGCTTAATACTAAG

TCTCGAAATAGCGTTGTTTATGTTAACTTTGGGAGCATAACAATAATGA

CCACGGCACAGCTTTTGGAGTTTGCTTGGGGTTTGGCGGCAACGGGAAA

GGAGTTTCTATGGGTGATGCGGCCGGATTCAGTAGCCGGAGAGGAGGCA

GTGATTCCAAAAGAGTTTTTAGCGGAGACAGCTGATCGAAGAATGCTGA

CAAGTTGGTGTCCTCAGGAGAAAGTTCTTTCTCATCCGGCGGTCGGAGG

GTTCTTGACCCATTGCGGGTGGAATTCGACGTTAGAAAGTCTTTCATGC

GGAGTTCCAATGGTATGTTGGCCATTTTTTGCTGAGCAACAAACAAATT

GTAAGTTTTCTTGTGATGAATGGGAGGTTGGTATTGAGATCGGTGGAGA

TGTCAAGAGGGGAGAGGTTGAGGCGGTGGTTAGAGAGCTCATGGATGGA

GAGAAAGGAAAGAAAATGAGAGAGAAGGCTGTAGAGTGGCGGCGCTTGG

CCGAGAAAGCTACAAAGCTTCCGTGTGGTTCGTCGGTGATAAATTTTGA

GACGATTGTCAACAAGGTTCTCTTGGGAAAGATCCCTAACACGTAA

CACC-NdeI-UGT85A3-Fw:

(SEQ ID NO: 6)
5'-CACCCATATGGGATCCCGTTTTGTTTC-3'

XhoI-stop-UGT85A3-Rv:

(SEQ ID NO: 7)
5'-CTCGAGTTACGTGTTAGGGATCTTTC-3'

A PCR reaction solution (50 µl) was prepared to consist of *Arabidopsis thaliana* petal-derived cDNA (1 µl), 1×Ex-Taq buffer (TaKaRaBio), 0.2 mM dNTPs, primers (0.4 pmol/µl each) and ExTaq polymerase (2.5 U). The PCR reaction was accomplished by incubation at 94° C. for 3 minutes and the subsequent amplification in which reactions at 94° C. for 1 minute, at 50° C. for 1 minute and at 72° C. for 2 minutes were repeated for 30 cycles in total. The PCR products were electrophoresed on a 0.8% agarose gel and stained with ethidium bromide, thereby resulting in an amplified band at a size of approximately 1.4 kb predicted from each template DNA.

These PCR products were subcloned into pENTR-TOPO Directional vector (Invitrogen) in accordance with the method recommend by the manufacturer. The clones were analyzed with a DNA Sequencer model 3100 (Applied Biosystems) by primer walking with synthetic oligonucleotide primers, thus confirming that there was no PCR-induced mutation in the inserted fragment.

A UGT85A3 fragment of approximately 1.4 kb was excised by means of the NdeI and XhoI restriction enzyme sites added to the primers and ligated to the NdeI and XhoI sites of an *E. coli* expression vector, pET15b (Novagen), to thereby obtain an *E. coli* expression vector for this enzyme gene. This vector was designed to carry the open reading frame of the UGT85A3 gene in frame with a His tag located upstream of the NdeI site of this vector so as to express a chimeric protein fused between UGT85A3 and the His tag.

Example 3

Enzyme Expression and Purification

To clarify biochemical functions of this enzyme, this enzyme was allowed to be expressed in *E. coli* cells. The UGT85A3 *E. coli* expression plasmid obtained above was used to transform *E. coli* strain BL21(DE3) in a standard manner. The resulting transformant was cultured overnight at 37° C. under shaking conditions in 4 ml of a 50 µg/ml ampicillin-containing LB medium (10 g/l typtone pepton, 5 g/l yeast extract, 1 g/l NaCl). After reaching the resting phase, the cultured solution (4 ml) was inoculated into a medium of the same composition (80 ml) and cultured at 37° C. under shaking conditions. At the time point where the cell turbidity (OD600) reached about 0.5, IPTG was added at a final concentration of 0.5 mM, followed by culturing at 18° C. for 20 hours under shaking conditions.

The following manipulations were all performed at 4° C. The cultured transformant was collected by centrifugation (5,000×g, 10 min) and then added to and suspended in Buffer S [20 mM HEPES buffer (pH 7.5), 20 mM imidazole, 14 mM β-mercaptoethanol] at 1 ml/g cell. Subsequently, the suspension was homogenized by ultrasonication (15 sec, repeated 8 times) and then centrifuged (15,000×g, 15 min). The resulting supernatant was collected as a crude enzyme solution. The crude enzyme solution was loaded onto a His SpinTrap column (GE Healthcare) which had been equilibrated with Buffer S, followed by centrifugation (70×g, 30 sec). After washing with the buffer, proteins bound to the column were eluted stepwise with 5 ml each of Buffer S containing 100 mM and 500 mM imidazole. Each elution fraction was subjected to buffer replacement with 20 mM HEPES buffer (pH 7.5), 14 mM (β-mercaptoethanol through a Microcon YM-30 unit (Amicon) (magnification of dialysis: ×1000).

Figure 4:
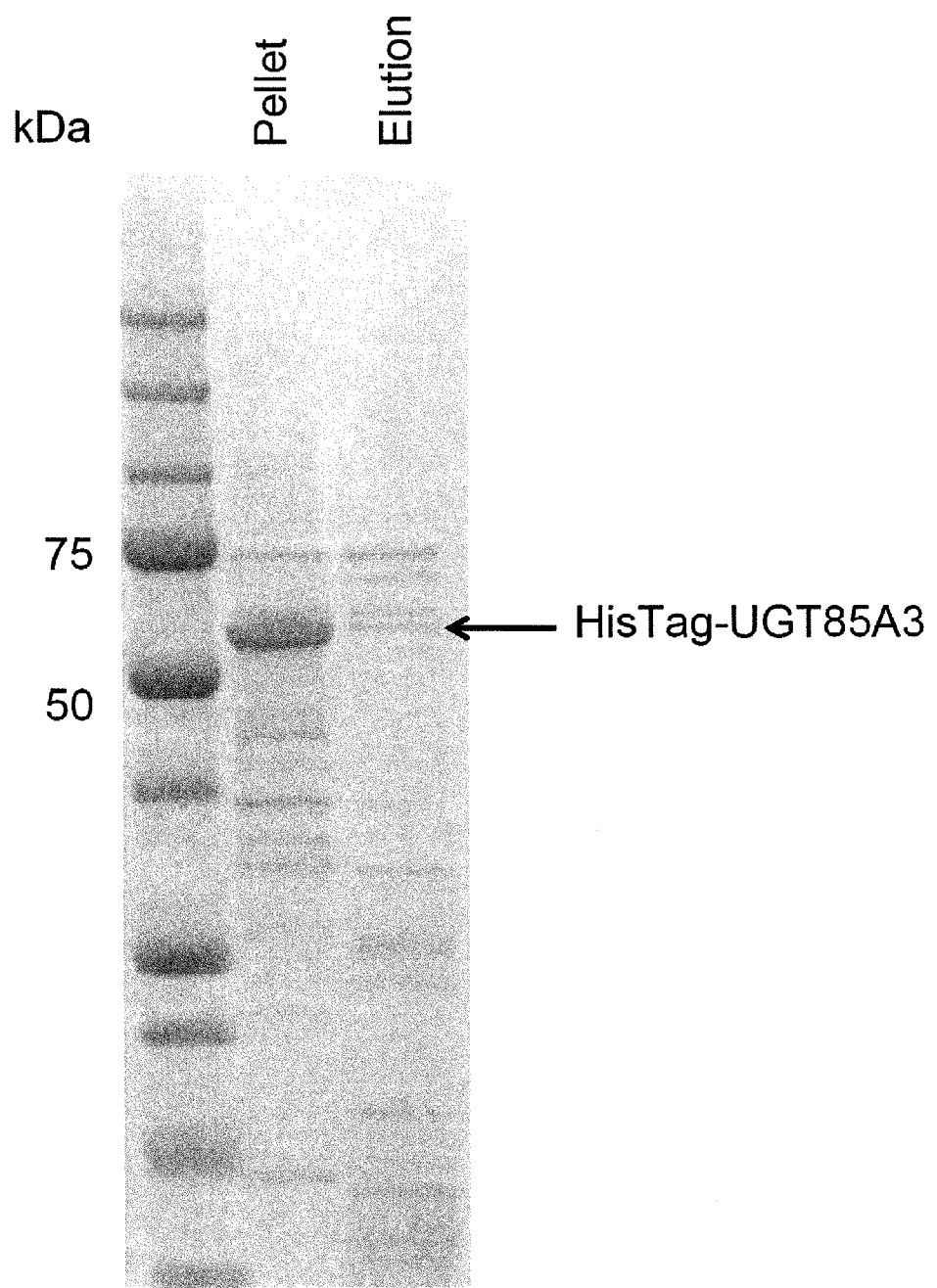
FIG. 4 shows the SDS-PAGE results obtained for a HisTag-UGT85A3 chimeric protein expressed in *E. coli* cells. The arrow in the figure indicates the HisTag-UGT85A3 chimeric protein.

As a result of SDS-PAGE separation and the subsequent CBB staining, in the fraction eluted with 200 mM imidazole, a protein was confirmed at approximately 56.7 kDa, which is the putative molecular weight for the HisTag-fused UGT85A3 chimeric protein. This fraction was used for enzyme analysis (FIG. 4).

Example 4

Activity Measurement

Standard enzyme reaction conditions are as follows. A reaction solution (2 mM UDP-glucose, 1.5 mM sugar acceptor substrate, 100 mM potassium phosphate buffer (pH 7.5), 25 µl purified UGT85A3 enzyme solution) was prepared in a volume of 50 µl with distilled water and reacted at 30° C. for 1 hour.

The enzyme reaction solution (5 µl) was analyzed by LC-MS under the following conditions.
LC Conditions
Column: CAPCELL PAK C18-UG120 (2.0 mm I.D.×150 mm)
Mobile phase: A: water (containing 0.05% formic acid), B: acetonitrile
Gradient: linear concentration gradient of B from 15% to 90% over 15 minutes
Flow rate: 0.2 ml per minute
Column oven: 40° C.
MS Conditions
ESI (negative mode)
SIM mode: (m/z 315, 338, 361, 363, 331, 354, 377, 429, etc.)

FIG. 5 shows information on products which are considered to be produced upon reaction with 4 types of monoterpenes (geraniol, 8-hydroxygeraniol, linalool and 8-hydroxylinalool).

Figure 6:
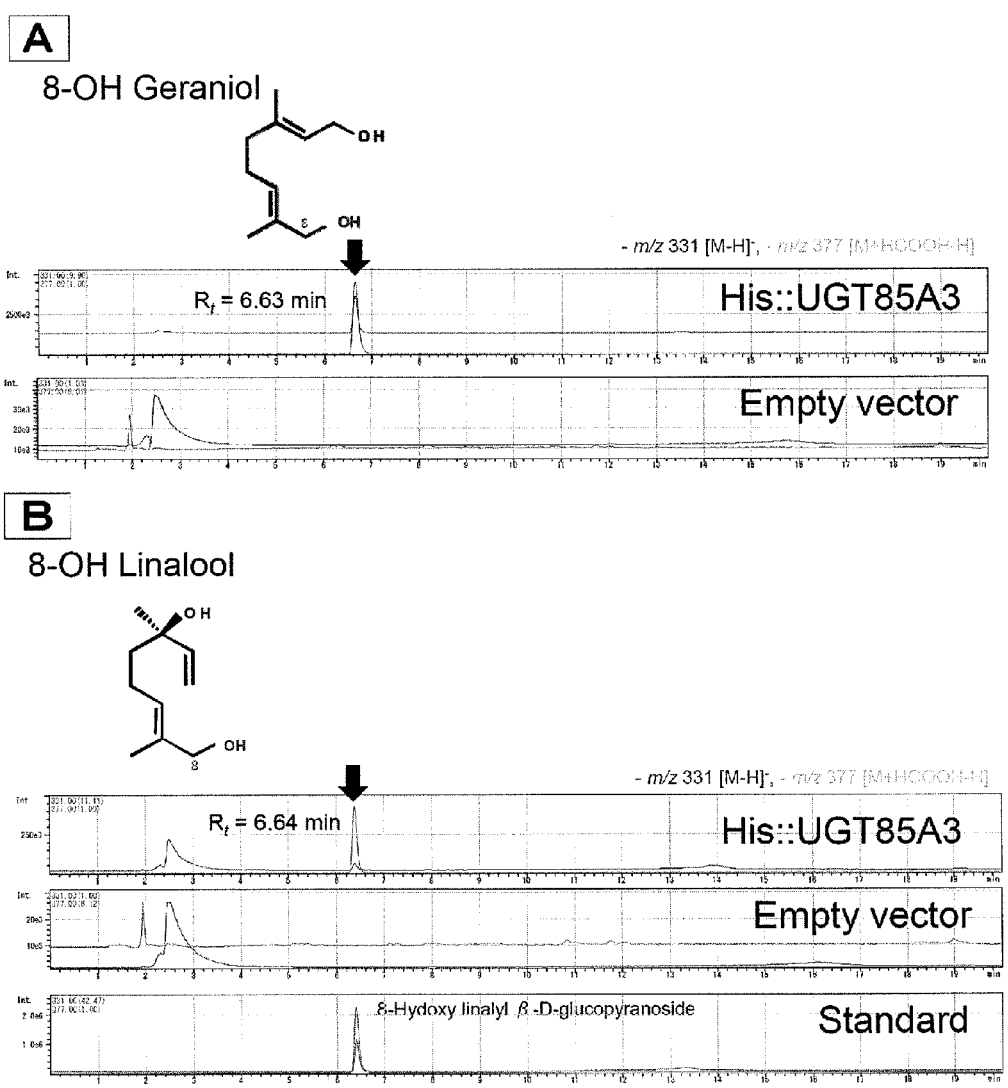
FIG. 6 shows the glycosylation activity of UGT85A3 on 8-hydroxygeraniol (FIG. 6A) and 8-hydroxylinalool (FIG. 6B) (LC-MS charts). The arrows each indicate a product (terpene glycoside) peak.
Figure 7:
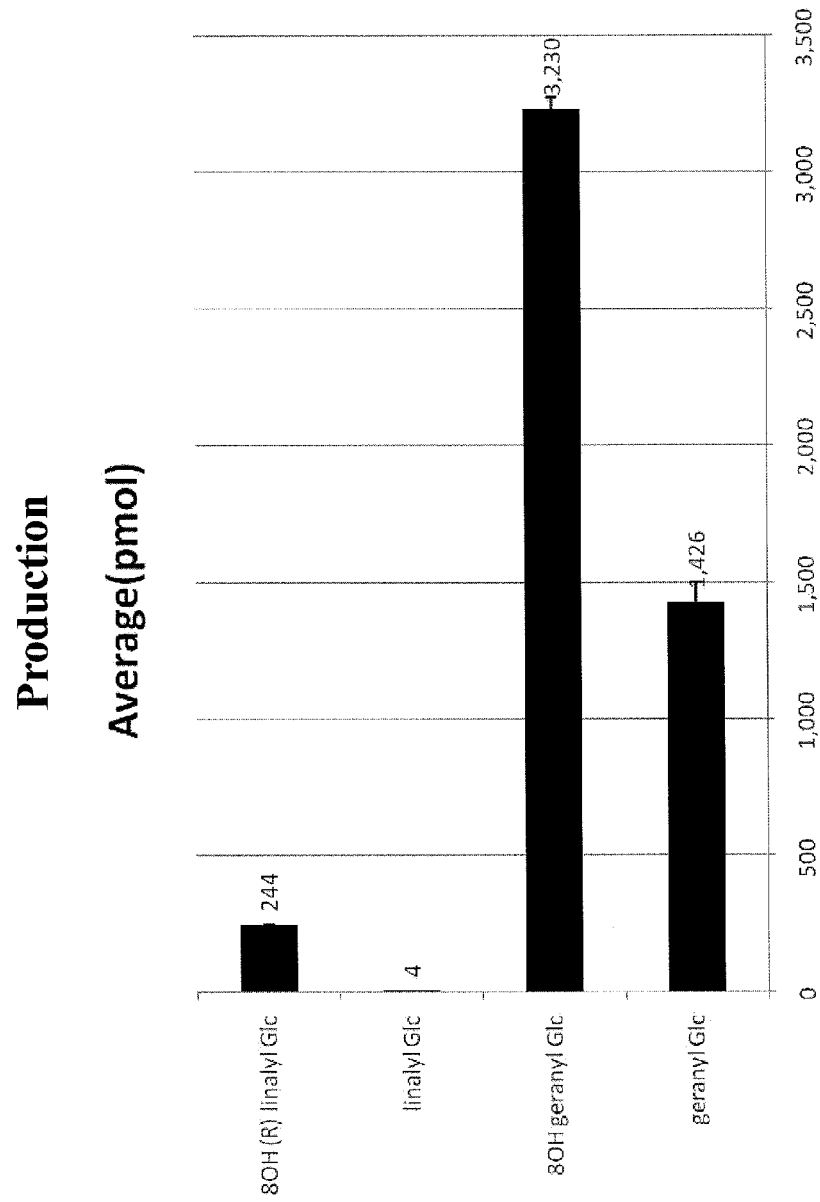
FIG. 7 shows the yields of geraniol, 8-hydroxygeraniol, linalool and 8-hydroxylinalool generated by UGT85A3 and comparison of the yields.
Figure 8:
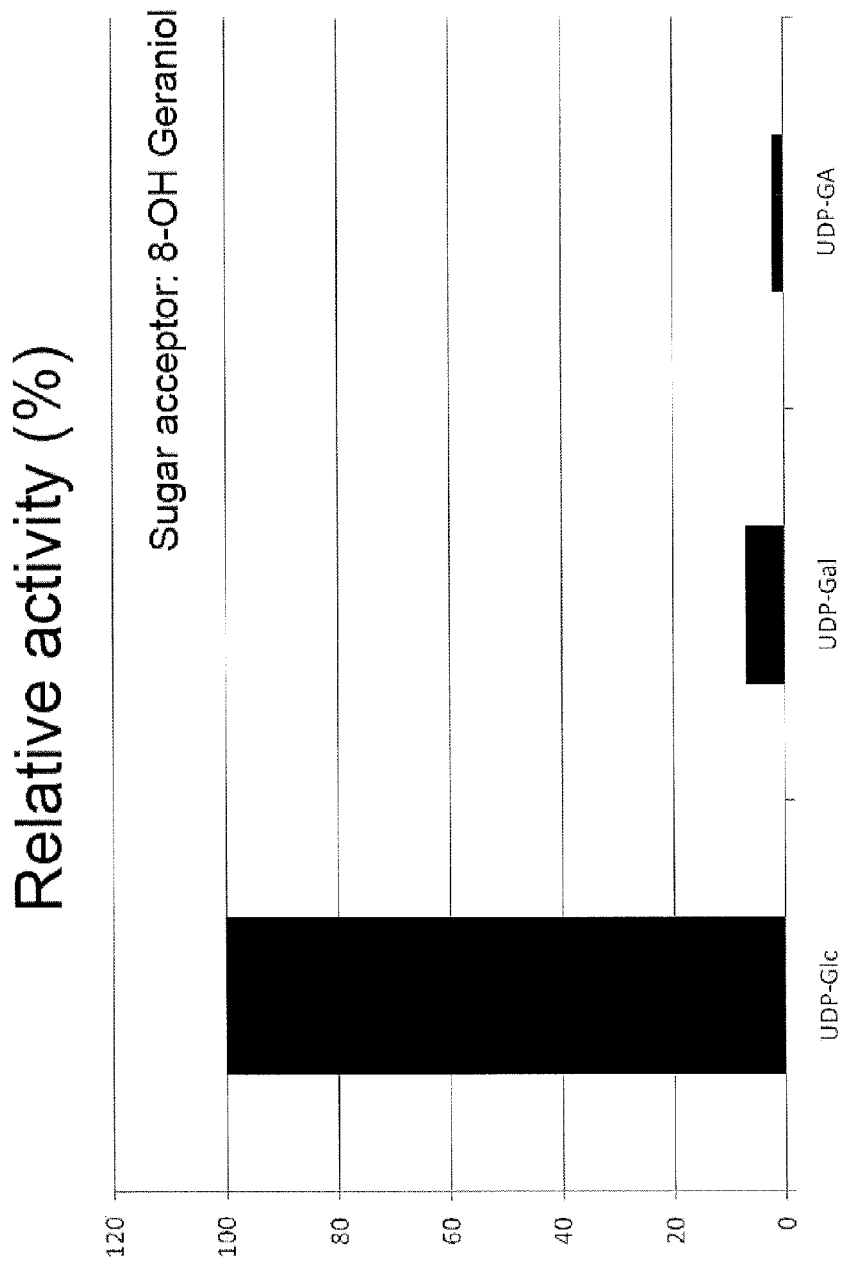
FIG. 8 shows the sugar donor selectivity of UGT85A3 (relative activity). The activity on UDP-glucose, which is the highest activity, is set to 100%.

As a result of analysis on these enzyme reaction solutions, a peak with a molecular weight suggesting addition of one glucose molecule was obtained for each of 8-hydroxygeraniol and 8-hydroxylinalool (FIG. 6A and FIG. 6B). The retention times of these peaks were in agreement with those of synthetic standards of geraniol monoglucoside and linalool 8-O-monoglucoside. These peaks were not observed in empty vector controls, thus confirming that they were provided by the action of UGT85A3. Further, in both cases of geraniol and linalool, higher activity was observed on their 8-hydroxylated forms (FIG. 7), thus indicating that UGT85A3 was glycosyltransferase having high specificity for the hydroxyl group at the 8-position of monoterpenes. To clarify the sugar donor selectivity of this enzyme, reaction with UDP-galactose or UDP-gluconic acid was attempted using 8-hydroxygeraniol as a sugar acceptor. As a result, these sugar donors yielded products at levels less than 1/10 of those in UDP-glucose (FIG. 8). It was therefore indicated that this enzyme was glucosyltransferase using UDP-glucose as a sugar donor.

When further studied for substrate specificity, this enzyme was found to have glycosylation activity on terpineol, nerolidol and citronellol. However, this enzyme showed no glycosylation activity on phenylpropanoid-derived secondary metabolites such as flavanone (Naringenin), flavonol (Quercetin), flavone (Apigenin), stilbene (Resveratrol) and coumarin (Esculetin).

In view of the foregoing, UGT85A3 was identified as a glycosyltransferase gene highly specific for the 8-position of terpenes, particularly monoterpenes. It is strongly suggested that this enzyme would be involved in glycosylation of 8-hydroxylated monoterpenes primarily in petals of *Arabidopsis thaliana*. Although there have been few reports on the functions of UGT85 family glycosyltransferases, UGT85A1 in *Arabidopsis thaliana* has been known to transfer in vitro one glucose molecule to the hydroxy group on trans-zeatin or hydrozeatin, both of which are molecular species of the plant hormone cytokinin (Non-patent Document 14). Moreover, UGT85B1 in sorghum (*Sorghum bicolor*) has been known to have the ability to transfer one glucose molecule to p-hydroxymandelonitrile to thereby generate a cyanogenetic glycoside, Dhurrin (Non-patent Document 15). Likewise, UGT85A19 has been reported as glycosyltransferase for cyanogenetic glycosides in almond (*Prunus dulcis*) (Non-patent Document 16). The activity on 8-hydroxylated monoterpenes found in the present invention can therefore be regarded as a novel enzyme activity in the UGT85 family.

Example 5

UGT85A1

Figure 9:
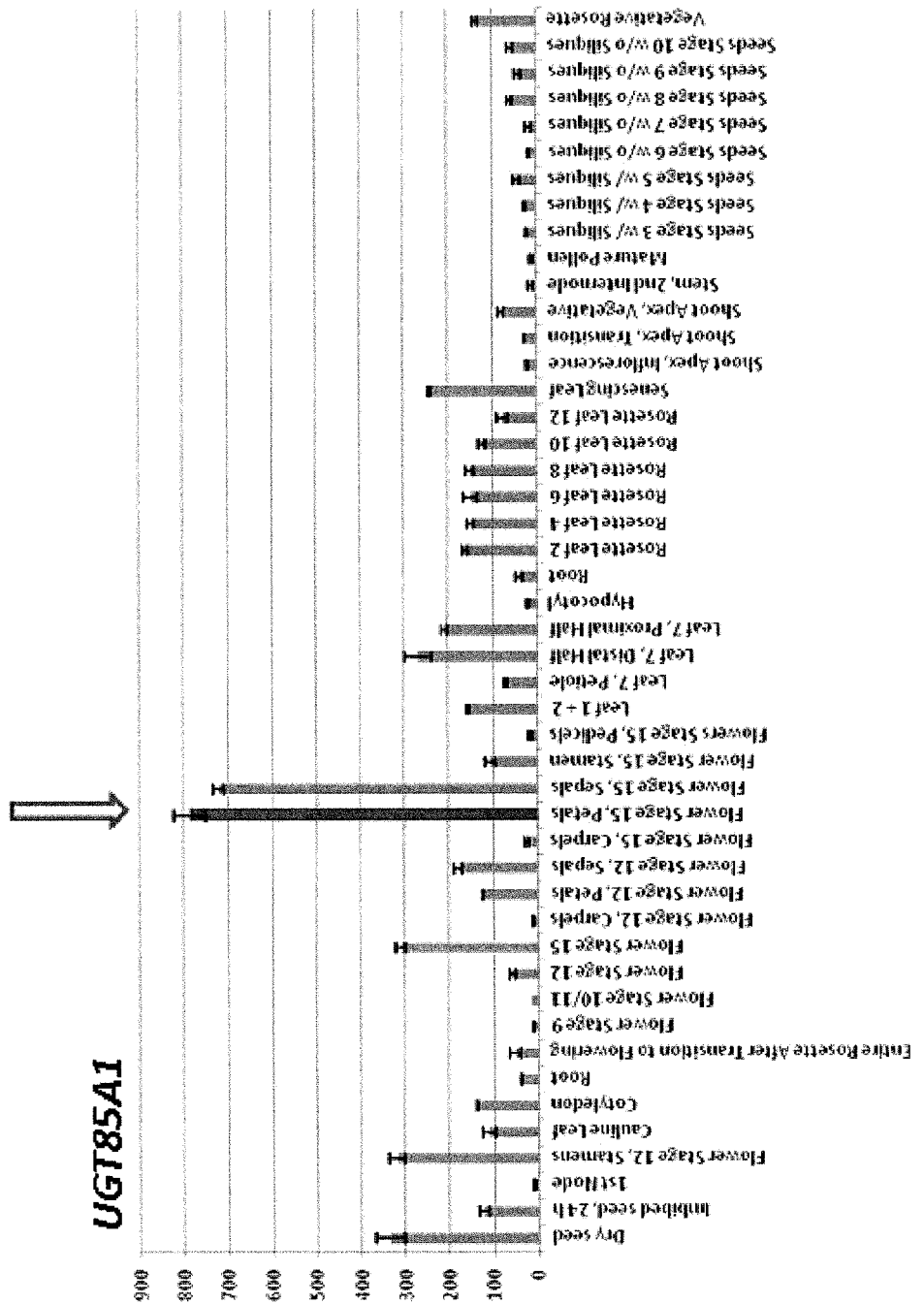
FIG. 9 shows the gene expression profiles of UGT85A1 in different organs. The arrow in the figure indicates expression in petals.

As genes belonging to the same subfamily as UGT85A3 which was found to show glycosylation activity on monoterpenes, at least 6 molecular species (UGT85A1, A2, A3, A4, A5 and A7) have been found in the genome of *Arabidopsis thaliana*. For analysis of gene expression in each organ of *Arabidopsis thaliana*, Arabidopsis eFB Browser (http://bbc.botany.utoronto.ca/efp/cgi-bin/efpWeb.cgi) was used to conduct *Arabidopsis thaliana* gene co-expression analysis (ATTED-II), thus confirming that UGT85A1 sharing the highest homology with UGT85A3 was also strongly expressed in petals, as in the case of UGT85A3 (FIG. 9: arrow). The CDS sequence encoding UGT85A1 and its deduced amino acid sequence are shown in SEQ ID NOs: 8 and 9, respectively.

Next, a HisTag-fused protein was also expressed for UGT85A1 in *E. coli* cells in the same manner as shown in Examples 1 to 3 above. Gene amplification for vector construction was performed with the following PCR primer set (SEQ ID NOs: 12 and 13).

```
NdeI-AtUGT85A1-Fw
                                    (SEQ ID NO: 12)
5'-CACCCATATGGGATCTCAGATCATTCATAAC-3'

BamHI-AtUGT85A1-Rv
                                    (SEQ ID NO: 13)
5'-GGATCCTTAATCCTGTGATTTTTGTCCCAAAAG-3'
```

Figure 10:
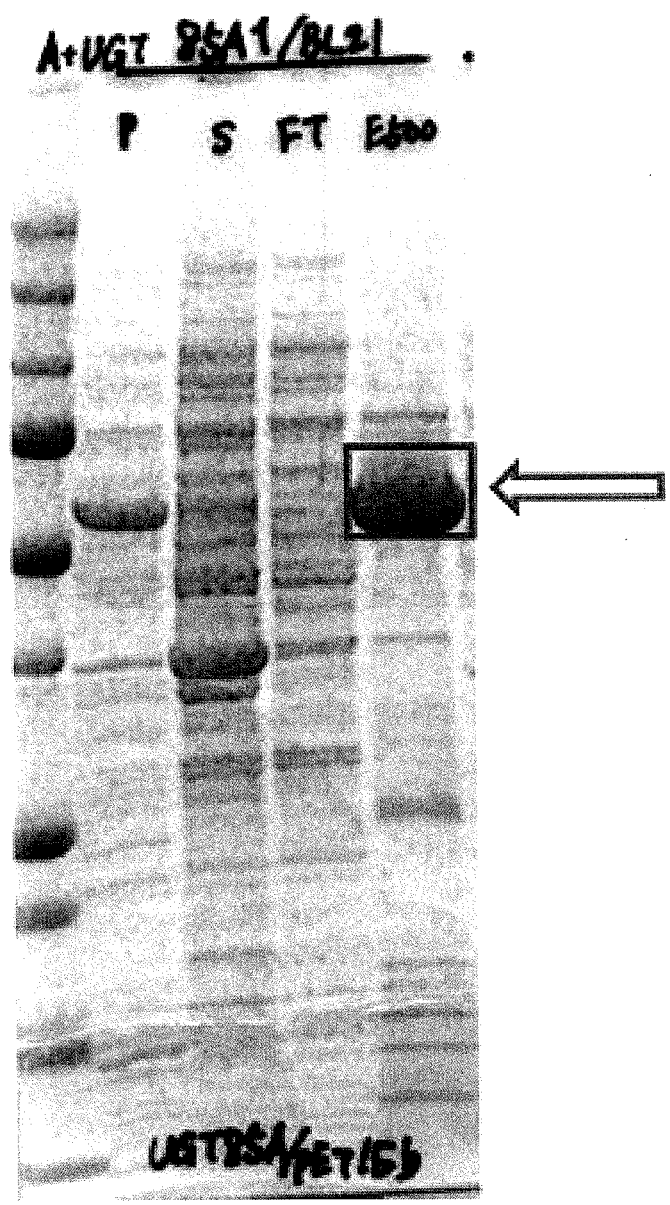
FIG. 10 shows the SDS-PAGE results obtained for a HisTag-UGT85A1 chimeric protein expressed in *E. coli* cells. The arrow in the figure indicates the HisTag-UGT85A1 chimeric protein.

After purification, expressed proteins were confirmed by SDS-PAGE (FIG. 10). In FIG. 10, the arrow indicates a recombinant UGT85A1 protein detected at approximately 50 KDa, while P, S, FT and E500 represent the precipitate, the soluble fraction, the fraction passing through the column and the eluted fraction, respectively. Moreover, in FIG. 10, the boxed area indicates the eluted HisTag-fused UGT85A1 protein.

Figure 11:
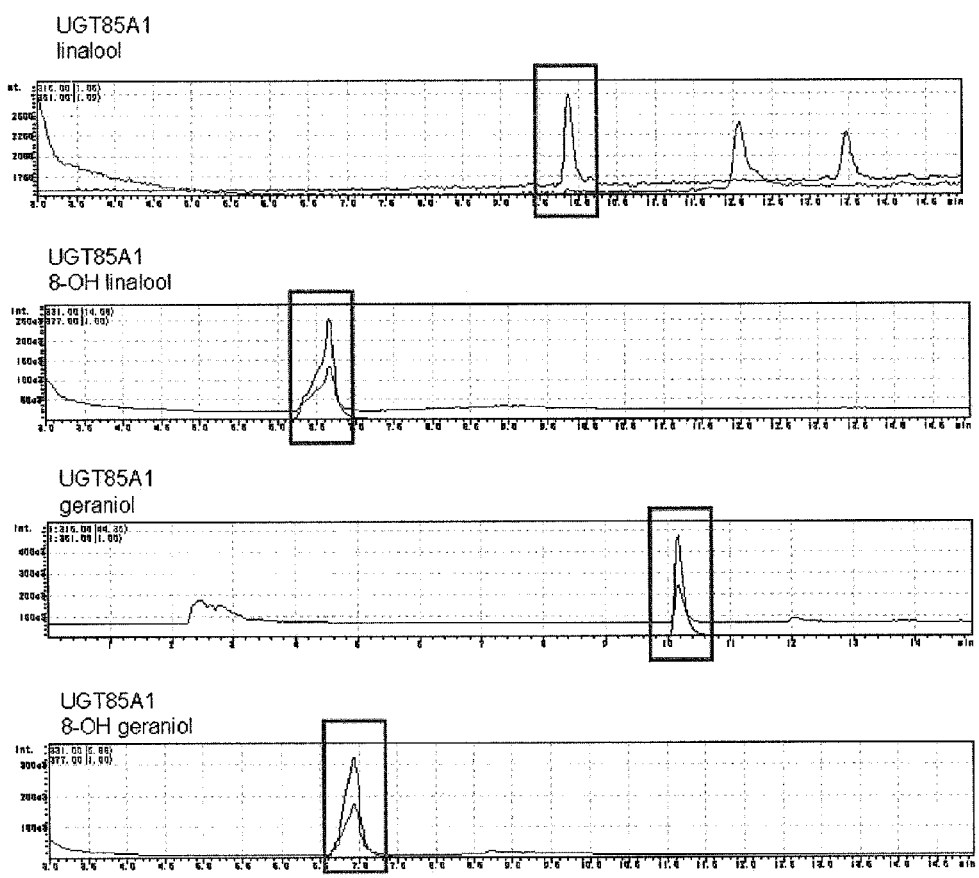
FIG. 11 shows the glycosylation activity of UGT85A1 on linalool, 8-hydroxylinalool, geraniol and 8-hydroxygeraniol (LC-MS charts). The boxed peaks each represent a product (terpene glycoside) peak.
Figure 12:
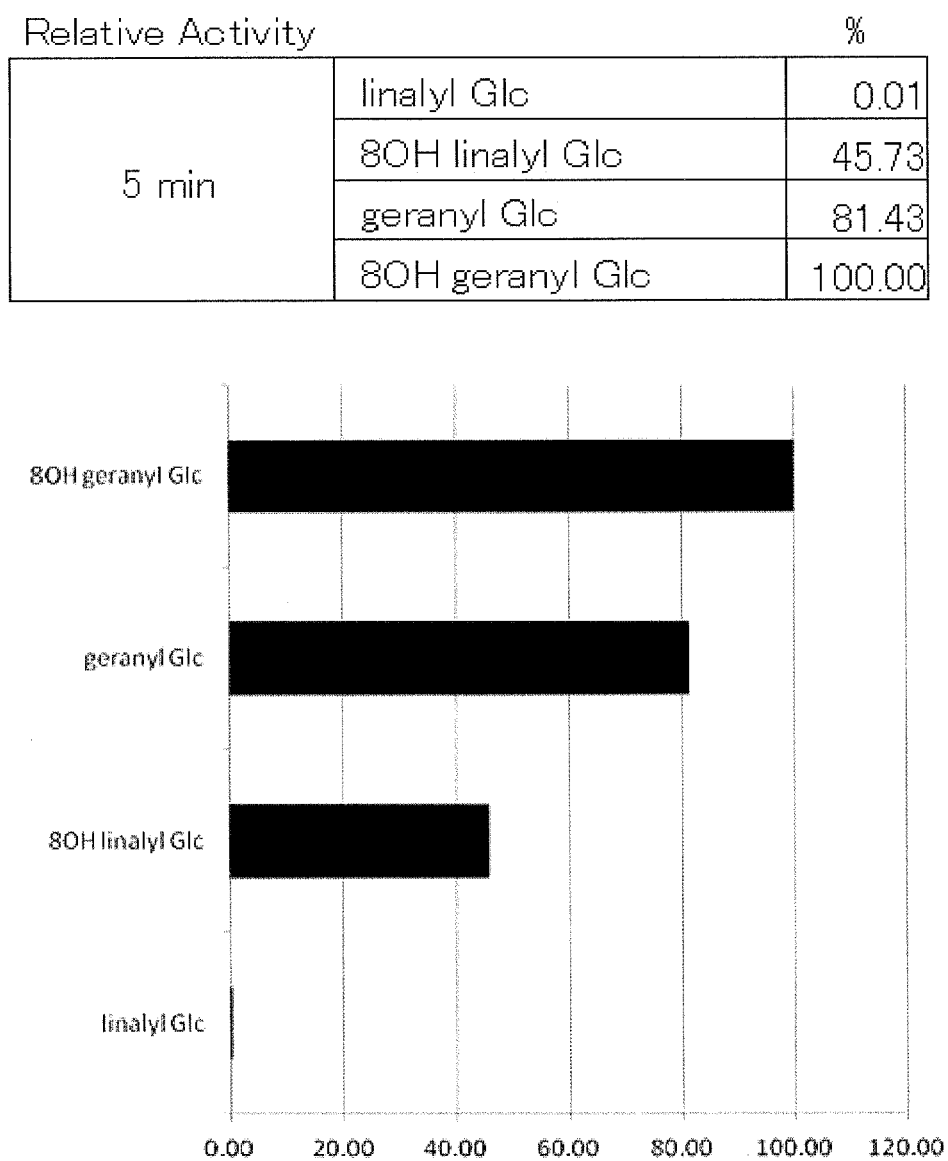
FIG. 12 shows the sugar acceptor selectivity of UGT85A1 (relative activity). The activity on 8-hydroxygeraniol, which is the highest activity, is set to 100%.

In the same manner as shown in Example 4, linalool, 8-hydroxylinalool, geraniol and 8-hydroxygeraniol were used as sugar acceptors for activity measurement. The four panels in FIG. 11 show the MS analysis chromatograms obtained for linalool, 8-hydroxylinalool, geraniol and 8-hydroxygeraniol (in this order from the top) which were used as sugar acceptors for reaction with UGT85A1. Linalool and geraniol appeared at m/z 315 [M-H], while their formic acid adducts were detected at m/z 361. 8-Hydroxylinalool and 8-hydroxygeraniol appeared at m/z 331 [M-H], while their formic acid adducts were detected at m/z 377. The boxed areas each indicate a product peak in each reaction solution. For all the monoterpene compounds, glycosylated products were detected (FIG. 11). However, the relative activity on these sugar acceptors measured per unit reaction time (5 minutes) indicated that UGT85A1 had very low relative activity on linalool and showed higher selectivity for geraniol than linalool, and particularly had higher activity on their 8-hydroxylated forms, as in the case of UGT85A3 (FIG. 12). These results of relative activity indicated that this enzyme had higher specificity for primary alcohols such as geraniol and 8-hydroxylated monoterpenes than for tertiary alcohols such as linalool.

The above results indicated that two types of *Arabidopsis thaliana* glycosyltransferases UGT85A1 and UGT85A3 resembling in their structure and expression pattern had glycosylation activity on monoterpenes and particularly caused glycosylation selectively on the hydroxyl group at the 8-position. In *Arabidopsis thaliana*, monoterpene alcohols appear to be accumulated in the form of 8-glycosides (Non-patent Document 1), and hence this enzyme giving 8-glycosylated monoterpene compounds would catalyze their reaction.

INDUSTRIAL APPLICABILITY

According to the present invention, one glucose molecule can be transferred to monoterpenes in vitro or by introducing the gene of the present invention into host cells, and hence the present invention is very useful in allowing more simple production or reduction of terpene glycosides, which may contribute to development of novel functional food materials and/or molecular breeding of secondary metabolites, etc.

SEQUENCE LISTING FREE TEXT

SEQ ID NO: 6: synthetic DNA
SEQ ID NO: 7: synthetic DNA
SEQ ID NO: 12: synthetic DNA
SEQ ID NO: 13: synthetic DNA

The invention claimed is:

1. A method for producing a monoterpene 8-glycoside, which comprises:
   (i) reacting a protein of any one selected from the group consisting of (a) to (c) shown below, a UDP-sugar, and a monoterpene compound to cause glycosylation at the 8-position of the monoterpene compound; wherein the monoterpene compound is 8-hydroxygeraniol or 8-hydroxylinalool:
   (a) a protein which consists of the amino acid sequence shown in SEQ ID NO: 2 or 9;
   (b) a protein which consists of an amino acid sequence with deletion, substitution, insertion and/or addition of 1 to 10 amino acids in the amino acid sequence shown in SEQ ID NO: 2 or 9 and which has glycosylation activity on the 8-position of a monoterpene compound; and
   (c) a protein which has an amino acid sequence sharing a sequence identity of 90% or more with the amino acid sequence shown in SEQ ID NO: 2 or 9 and which has glycosylation activity on the 8-position of a monoterpene compound; and
   (ii) purifying the 8-glycoside of the monoterpene compound generated in step (i).

2. The method according to claim 1, wherein the UDP-sugar is UDP-glucose.

3. A non-human transformant transformed with a polynucleotide of any one selected from the group consisting of (a) to (e):
   (a) a polynucleotide containing the nucleotide sequence shown in SEQ ID NO: 1, 3, 8 or 10;
   (b) a polynucleotide encoding a protein which consists of the amino acid sequence shown in SEQ ID NO: 2 or 9;
   (c) a polynucleotide encoding a protein which consists of an amino acid sequence with a deletion, substitution, insertion and/or addition of 1 to 10 amino acids in the amino acid sequence shown in SEQ ID NO: 2 or 9 and which has glycosylation activity on the 8-position of a monoterpene compound; and
   (d) a polynucleotide encoding a protein which has an amino acid sequence sharing a sequence identity of 90% or more with the amino acid sequence shown in SEQ ID NO: 2 or 9 and which has glycosylation activity on the 8-position of a monoterpene compound.

4. The transformant according to claim 3, which contains the nucleotide sequence shown in SEQ ID NO: 1, 3, 8 or 10.

5. The transformant according to claim 3, wherein the polynucleotide is inserted into an expression vector.

6. The transformant according to claim 3, which is a plant.

7. An extract of the transformant according to claim 3, wherein the extract is prepared by homogenizing the transformant to obtain a homogenate, centrifuging the homogenate to obtain a supernatant, and collecting the supernatant as the extract.

8. A food, an aromatic, a pharmaceutical preparation or an industrial raw material, which comprises the extract according to claim 7.

9. A method for producing a protein having glycosylation activity on the 8-position of a monoterpene compound, which comprises culturing the non-human transformant according to claim 3, wherein the monoterpene compound is 8-hydroxygeraniol or 8-hydroxylinalool.

* * * * *